United States Patent [19]

Nielsen et al.

[11] Patent Number: 5,324,711

[45] Date of Patent: Jun. 28, 1994

[54] ARYLOXY BENZOTRIAZOLE HERBICIDAL AGENTS AND METHODS FOR THE PREPARATION THEREOF

[75] Inventors: Donald R. Nielsen, Wadsworth, Ohio; Thomas A. Lies, Princeton, N.J.

[73] Assignee: American Cyanamid Company, Wayne, N.J.

[21] Appl. No.: 415,953

[22] Filed: Oct. 5, 1989

Related U.S. Application Data

[63] Continuation-in-part of Ser. No. 266,545, Nov. 3, 1988, abandoned.

[51] Int. Cl.$^5$ .................................. A01N 43/64
[52] U.S. Cl. .................................. 504/261; 504/253; 546/271; 548/259
[58] Field of Search ............ 548/260, 259, 261; 71/92; 504/261

[56] References Cited

U.S. PATENT DOCUMENTS

| | | | |
|---|---|---|---|
| 3,508,318 | 4/1970 | Schellhamer | 548/259 |
| 4,086,242 | 4/1978 | Diehl et al. | 71/92 |
| 4,129,521 | 12/1978 | Stroebel | 548/260 |
| 4,213,774 | 7/1980 | Schurter | 71/92 |
| 4,240,822 | 12/1980 | Diehl et al. | 548/259 |
| 4,377,708 | 3/1983 | Steffens | 71/92 |
| 4,623,379 | 11/1986 | Baum | 71/92 |
| 4,668,278 | 5/1987 | Haga | 548/260 |
| 4,911,754 | 3/1990 | Hunt et al. | 548/217 |

FOREIGN PATENT DOCUMENTS

| | | |
|---|---|---|
| 0107216 | 5/1984 | European Pat. Off. |
| 0178708 | 4/1986 | European Pat. Off. |
| 0355049 | 2/1990 | PCT Int'l Appl. |
| 2157679 | 10/1985 | United Kingdom |

*Primary Examiner*—Donald G. Daus
*Attorney, Agent, or Firm*—Peggy Ann Climenson

[57] ABSTRACT

This invention is directed to certain substituted aryloxy benzotriazole compounds which are herbicidal agents.

The structures of these compounds are represented by formulas I and II shown below:

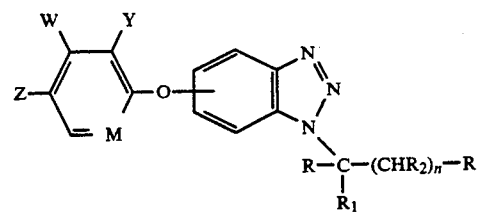

or

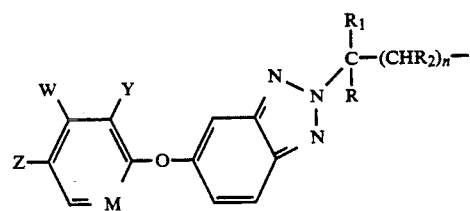

wherein
M is C—X, N or N$^+$—O$^-$;
W, X, Y and Z each independently represent hydrogen, halogen, nitro, cyano, $C_1$–$C_4$ haloalkyl or $C_1$–$C_4$ haloalkoxy;
n is 0, 1 or 2;
R is hydrogen, $C_1$–$C_4$ alkyl, aryl or when taken together with $R_1$, R and $R_1$ may form a ring in which $RR_1$ are represented by the structure —(CH$_2$)$_m$— where m is an integer of 2, 3, 4 or 5;
$R_1$ and $R_2$ are each independently hydrogen, $C_1$–$C_4$ alkyl or when taken together $R_1$ and $R_2$ may form a ring in which $R_1R_2$ are represented by the structure —(CH$_2$)$_m$— where m is an integer of 2, 3, 4 or 5;
$R_3$ is cyano,

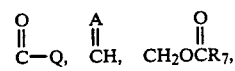

$CH_2OR_8$ or $CH(OR_9)_2$;
Q is OH, $OR_4$ or $NR_5R_6$;
A is O, $NOR_5$, $NCOR_5$, $NNR_5R_6$ or $NNHCONH_2$;

(Abstract continued on next page.)

$R_7$ is hydrogen, $C_1-C_4$ alkyl or aryl;
$R_8$ is hydrogen or $C_1-C_4$ alkyl;
$R_9$ is $C_1-C_4$ alkyl;
$R_4$ is $C_1-C_6$ alkyl optionally interrupted by O or S or optionally substituted with $C_1-C_4$ alkoxy, halogen, hydroxy, $C_3-C_6$ cycloalkyl, furyl, or optionally substituted phenyl; $C_3-C_6$ alkenyl optionally substituted with one or two $C_1-C_3$ alkoxy, halogen, substituted phenyl or $C_3-C_6$ cycloalkyl; $C_3-C_6$ alkynyl optionally substituted with $C_1-C_4$ alkoxy or halogen; $C_3-C_6$ cycloalkyl; ammonium; $C_1-C_6$ dialkylammonium; $C_1-C_6$ trialkylammonium; a metal cation; or a moiety of formula

$R_5$ and $R_6$ each independently represent hydrogen, $C_1-C_6$ alkyl, phenyl or halophenyl;
the benzotriazole N-oxide or N-methosulfate; and when $R_1$ or $R_2$ is $C_1-C_4$ alkyl, the optical isomer thereof; with the proviso that when M is C—X in formula I, wherein X is hydrogen, halogen, nitro, cyano or $C_1-C_4$ haloalkyl, the benzotriazole is substituted in the 6 position by aryloxy, n is 0, $R_3$ is

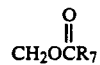

and $R_7$ is $C_1-C_4$ alkyl, then R and $R_1$ cannot be hydrogen or $C_1-C_4$ alkyl. The invention is further directed to methods for the preparation of the aryloxy benzotriazole compounds.

24 Claims, No Drawings

ARYLOXY BENZOTRIAZOLE HERBICIDAL AGENTS AND METHODS FOR THE PREPARATION THEREOF

This application is a continuation-in-part of U.S. application Ser. No. 266,545, filed on Nov. 3, 1988, now abandoned.

BACKGROUND OF THE INVENTION

Certain heteroaromatic diphenyl ethers are disclosed as herbicidal agents in European Patent Publication No. 178,708. The publication discloses certain substituted phenoxy benzoheteroaromatic compounds such as benzotriazoles, benzoxadiazoles, benzothiadiazoles, benzoxazoles and benzothiazoles as herbicides. It has now been found that when aryloxy benzotriazoles are substituted at the $N^1$ position by certain substituted alkyl moieties, an unexpectedly increased level of herbicidal activity is obtained.

SUMMARY OF THE INVENTION

The present invention is directed to certain substituted aryloxy benzotriazole compounds that are highly effective as herbicidal agents. The present invention is also directed to methods for preparing the aryloxy benzotriazole compounds.

The aryloxy benzotriazole compounds of the present invention have the structure:

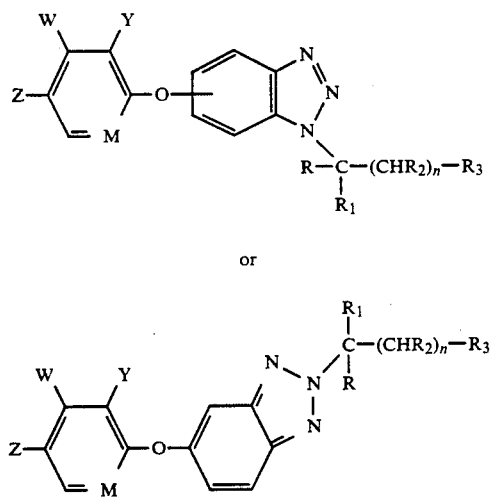

wherein
the benzotriazole portion of the formula I compound is substituted by aryloxy in the 5 or 6 position;
M is C—X, N, or $N^+$—$O^-$;
W, X, Y, and Z are each independently hydrogen, halogen, nitro, cyano, $C_1$-$C_4$ haloalkyl or $C_1$-$C_4$ haloalkoxy;
n is 0, 1 or 2;
R is hydrogen, $C_1$-$C_4$ alkyl, aryl or when taken together with $R_1$, R and $R_1$ may form a ring in which $RR_1$ are represented by the structure —$(CH_2)_m$— where m is an integer of 2, 3, 4 or 5;
$R_1$ and $R_2$ are each independently hydrogen, $C_1$-$C_4$ alkyl or when taken together $R_1$ and $R_2$ may form a ring in which $R_1R_2$ are represented by the structure —$(CH_2)_m$ where m is an integer of 2, 3, 4 or 5;
$R_3$ is cyano,

$CH_2OR_8$ or $CH(OR_9)_2$;
Q is OH, $OR_4$ or $NR_5R_6$;
A is O, $NOR_5$, $NCOR_5$, $NNR_5R_6$ or $NNHCONH_2$;
$R_7$ is hydrogen, $C_1$-$C_4$ alkyl or aryl;
$R_8$ is hydrogen or $C_1$-$C_4$ alkyl;
$R_9$ is $C_1$-$C_4$ alkyl;
$R_4$ is $C_1$-$C_6$ alkyl optionally interrupted by O or S or optionally substituted with $C_1$-$C_4$ alkoxy, halogen, hydroxy, $C_3$-$C_6$ cycloalkyl, furyl, or optionally substituted phenyl; $C_3$-$C_6$ alkenyl optionally substituted with one or two $C_1$-$C_3$ alkoxy, halogen, substituted phenyl or $C_3$-$C_6$ cycloalkyl; $C_3$-$C_6$ alkynyl optionally substituted with $C_1$-$C_4$ alkoxy or halogen; $C_3$-$C_6$ cycloalkyl; ammonium; $C_1$-$C_6$ dialkylammonium; $C_1$-$C_6$ trialkylammonium; a metal cation; or a moiety of formula

$R_5$ and $R_6$ each independently represent hydrogen, $C_1$-$C_6$ alkyl, phenyl or halophenyl;
the benzotriazole N-oxides and N-methosulfates; and
when $R_1$ or $R_2$ is $C_1$-$C_4$ alkyl, the optical isomers thereof.

Surprisingly, it has been found that the substituted aryloxy benzotriazoles are herbicidal agents, which exhibit control of a broad spectrum of monocotyledonous and dicotyledonous plants. The compounds are effective at low application rates for controlling weeds indigenous to both dry and wet land areas.

DETAILED DESCRIPTION OF THE INVENTION

A preferred group of the substituted aryloxy benzotriazoles of the present invention are illustrated by above formula I, wherein the benzotriazole is substituted in the 6 position by aryloxy; M is C—X; X, Y, and Z each independently represent Cl, F, or $CF_3$; W is hydrogen; n is O; R and $R_1$ are each independently hydrogen or methyl; and $R_3$ is $C_1$-$C_4$ carboalkoxy or carboxy.

Compounds of formula I (wherein the benzotriazole is substituted in the 5 or 6 position) or formula II are prepared as shown below i flow diagram I wherein B is halogen and M, W, Y, Z, n, R, $R_1$, $R_2$ and $R_3$ are as hereinabove described for formula I and II with the proviso that at least one or R or $R_1$ is hydrogen.

FLOW DIAGRAM I

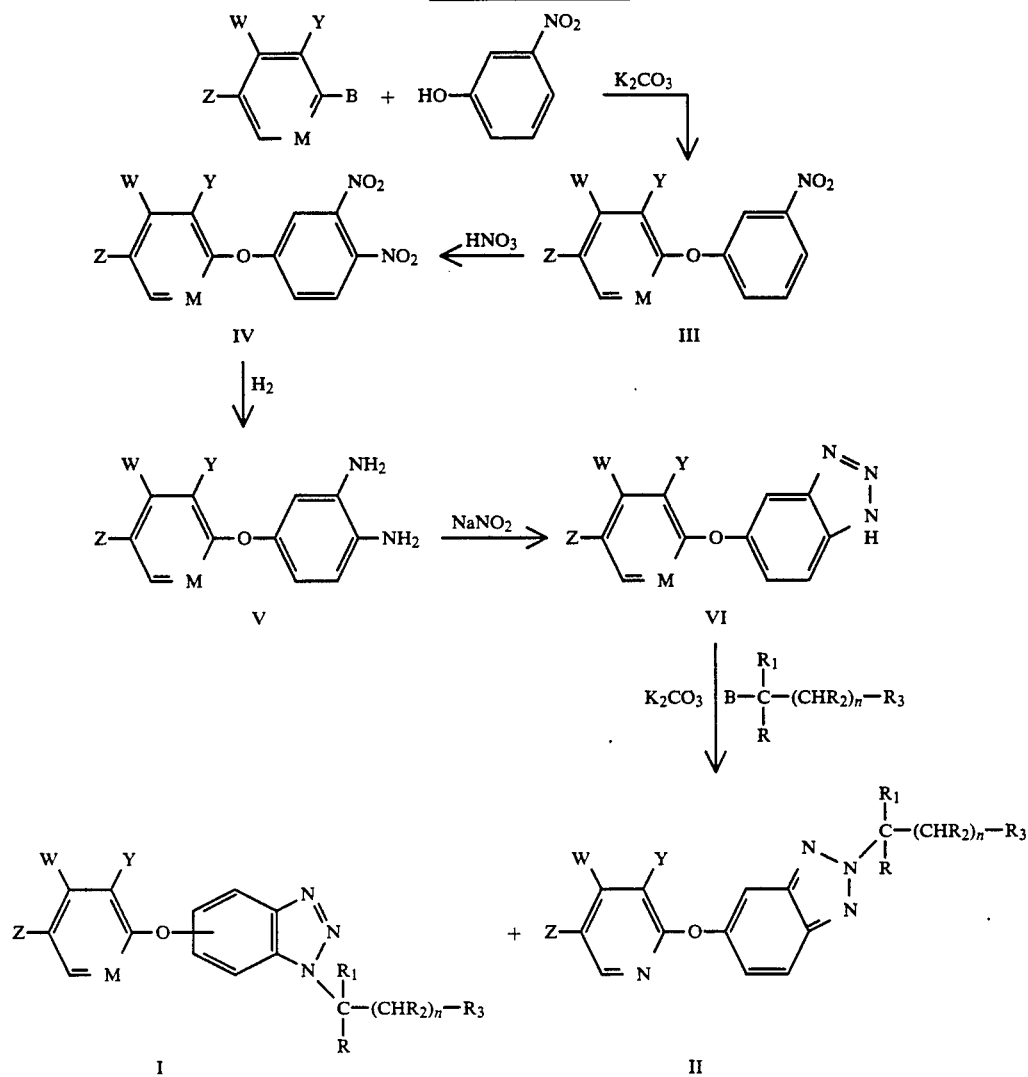

The appropriately substituted halobenzene is reacted with m-nitrophenol to give the phenyl ether III which is then nitrated to give compound IV, which in turn is reduced to give the diamino compound, V. The compound V is ring closed in the presence of sodium nitrite and the resultant phenoxy benzotriazole, VI, is reacted with a haloalkyl electrophile to yield compounds of formula I and II as shown above wherein at least one of R or $R_1$ is hydrogen.

Alternatively, the compounds of formula I, wherein the benzotriazole is substituted in position 6, are prepared as shown below in flow diagram II.

FLOW DIAGRAM II

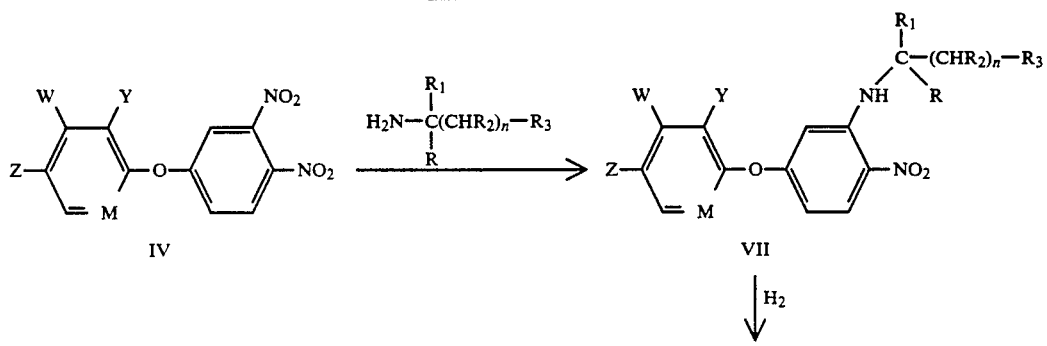

-continued
FLOW DIAGRAM II

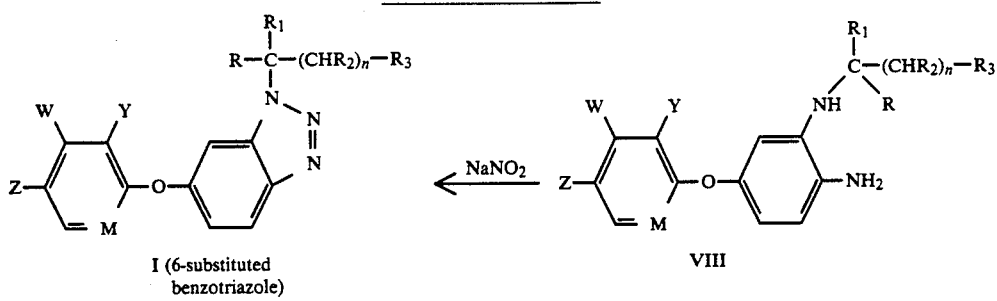

I (6-substituted benzotriazole)     VIII the appropriately substituted dinitro compound (IV) is reacted with an amine nucleophile to give compounds of formula VII. Reduction of VII affords the diamine VIII, which is ring-closed through the agency of sodium nitrite to afford compounds of formula I, wherein the aryloxy group is attached to position 6 of the benzotriazole. This method of preparation is most effectively carried out when n is O and $R_3$ is $CH(OR_9)_2$.

Another method useful for preparing compounds of formula I wherein the benzotriazole is substituted in position 6 is shown in flow diagram III.

FLOW DIAGRAM III

-continued
FLOW DIAGRAM III

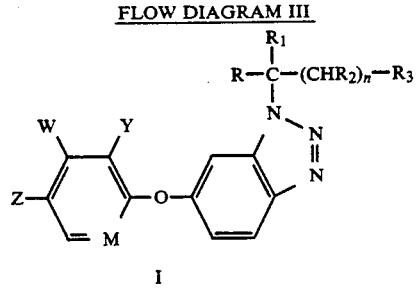

I

The appropriately substituted halobenzene is reacted with the 6-hydroxy benzotriazole compound IX to give compounds of formula I.

The intermediate 6-hydroxy benzotriazole compound IX wherein when n is O, $R_3$ is $CH(OR_9)_2$ is prepared as shown in flow diagram IV.

FLOW DIAGRAM IV

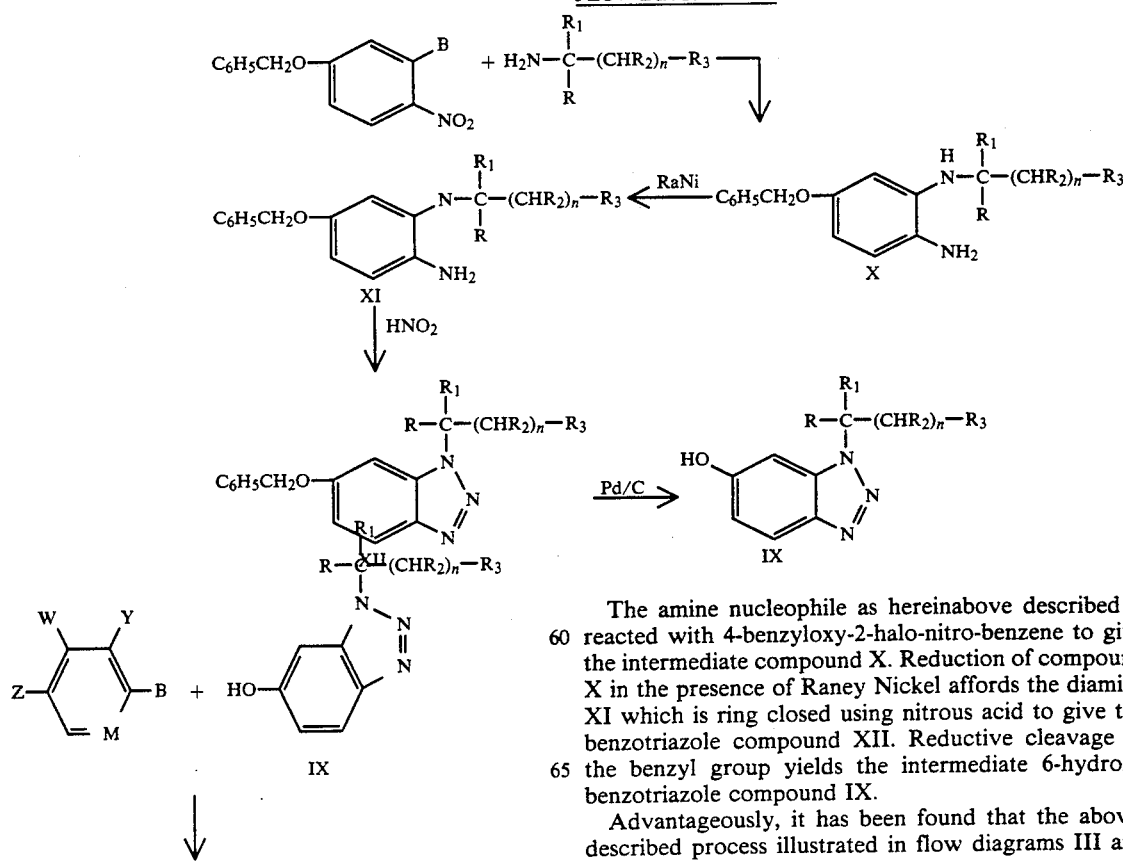

The amine nucleophile as hereinabove described is reacted with 4-benzyloxy-2-halo-nitro-benzene to give the intermediate compound X. Reduction of compound X in the presence of Raney Nickel affords the diamine XI which is ring closed using nitrous acid to give the benzotriazole compound XII. Reductive cleavage of the benzyl group yields the intermediate 6-hydroxy benzotriazole compound IX.

Advantageously, it has been found that the above-described process illustrated in flow diagrams III and IV is most effectively carried out for those formula I compounds wherein n is 0, and $R_3$ is carboxy when the amine nucleophile is protected as the dialkyl acetal of the corresponding aminoaldehyde. Subsequent hydrolysis and oxidation of the thus-obtained 6-aryloxy benzotriazole intermediate XIII affords compounds of formula I wherein n is 0 and $R_3$ is carboxy. An example of this process is shown in flow diagram V wherein the dimethyl acetal of an aminoacetaldehyde is used as the amine nucleophile.

bout 5% to 10% by weight of a nonionic surfactant such as an alkylphenoxy polyethoxy alcohol. This concentrate is dispersed in water for application as a liquid spray.

Preparation of a granular formulation is achieved by dissolving the active compound in a solvent such as methylene chloride, N-methylpyrrolidone, or the like and spraying the thus-prepared solution on a granular carrier such as corncob grits, sand, attapulgite or kaolin. The granular product, thus-prepared, generally com-

FLOW DIAGRAM V

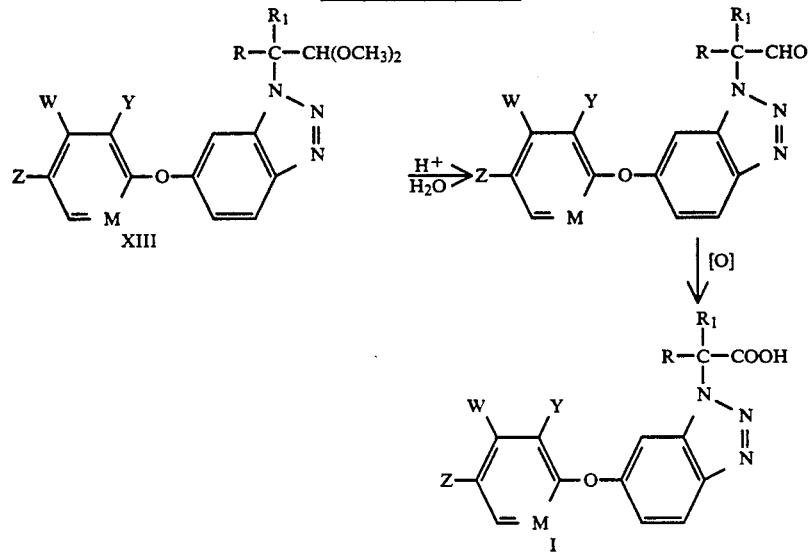

The formula I and II aryloxy benzotriazoles of the present invention are useful for the control of a wide variety of herbaceous and woody, annual and perennial, monocotyledonous and dicotyledonous plants. These compounds are effective in controlling the above-said plants when applied to the foliage thereof or to soil, or water, containing seeds or propagating organs of said plants such as tubers, rhizomes, or stolons at rates of about 0.005 to 5.0 kg/ha and preferably at rates of about 0.01 to 4.0 kg/ha.

Among the plants which may be controlled with the compounds of this invention are *Abutilon theophrasti, Sesbania exaltata, Ipomoea* Sp., *Sida spinosa, Cassia obtusifolia, Seteria glauca, Sorghum halepense,* and *Echinocholoa crusgalli.*

The formula I compounds are applied in agronomically acceptable carriers which are formulated as wettable powders, dust concentrates, granula formulations, suspension concentrates, microemulsions, emulsifiable concentrates, solutions, emulsions and the like.

Wettable powders are prepared by grinding together about 20% to 45% by weight of a finely divided solid carrier such as kaolin bentonite, diatomaceous earth, attapulgite, or the like, 45% to 80% by weight of the active compound, 2% to 5% by weight of a dispersing agent such as sodium lignosulfate, and 2% to 5% by weight of a nonionic surfactant such as octylphenoxy polyethoxy ethanol, nonylphenoxy polyethoxy ethanol or the like.

A typical emulsifiable concentrate is prepared by dissolving about 5% to 25% by weight of the active compound in about 65% to 90% by weight of a carrier such as N-methylpyrrolidone, isophorone, butyl cellosolve, methyl acetate or the like and dispersing therein prises about 3% to 20% by weight of the active compound and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight, all temperatures are expressed as degrees centigrade, NMR designates proton nuclear magnetic resonance spectroscopy, and HPLC designates high pressure liquid chromatography.

EXAMPLE 1

Preparation of 3-chloro-5-fluoro-4-(3-nitrophenoxy)benzotrifluoride

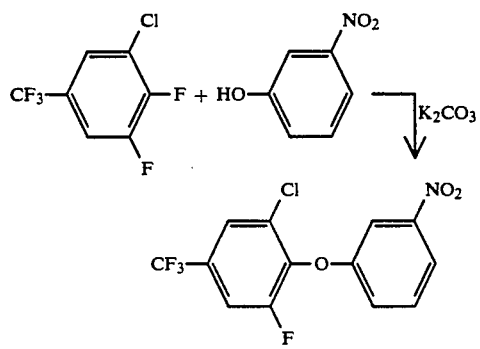

A mixture of 36.7 g of 3-nitrophenol, 54.1 g of 3,4-difluoro-5-chlorobenzotrifluoride, and 41.5 g of powdered potassium carbonate in 300 mL dimethylsulfoxide is stirred at room temperature for 16 hours, then at 50° C. for 5½ hours. The mixture is cooled, poured onto 1 L of water and extracted with methylene chloride. The organic phase is washed thoroughly with water, dried, and concentrated in vacuo to give 81.1 g of a residue, which is an isomeric mixture. Chromatography on silica gel using 7:3 hexane-ether as eluant affords 72.7 g of the desired product; HPLC analysis indicates >90% purity.

EXAMPLE 2

Preparation of
3-chloro-5-fluoro-4-(3,4-dinitrophenoxy)benzotrifluoride

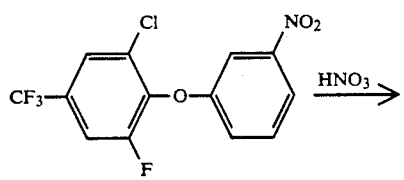

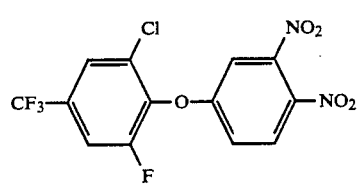

a solution of 72.7 g of 3-chloro-5-fluoro-4-(3-nitrophenoxy)benzotrifluoride in 200 mL of acetic acid is stirred at 10° C. and 108 g of 13% nitric acid in sulfuric acid is added over a 4 hour period. During the addition, more acetic acid is added so as to keep the reaction homogeneous. The reaction is stirred at room temperature for 21 hours, then 50 mL of acetic anhydride is added in 3 portions over 3 days with water bath cooling. The final reaction mixture is poured onto ice and extracted with methylene chloride. The combined extracts are washed with water followed by aqueous carbonate, then dried and concentrated in vacuo to give 73.5 g of a residue. This material is dissolved in 50 mL of acetic anhydride and cooled to 0° C. A solution of 8.5 mL of fuming nitric acid in 45 mL sulfuric acid is added alternately with 35 mL of acetic anhydride and 10 mL of acetic acid over a 4 hour period. After stirring for an additional one-half hour, the reaction is poured onto ice and worked up as above to afford 79 g of a residue. Column chromatography of this material on silica gel using hexane-chloroform mixtures affords 13.2 g of the title product as an oil, identified by NMR.

EXAMPLE 3

Preparation of
6-[(2-chloro-α,α,α,6-tetrafluoro-p-tolyl)oxy]-1H-benzotriazole

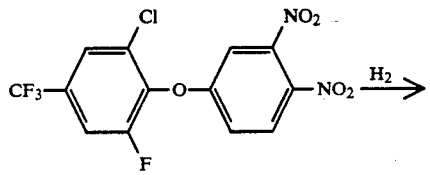

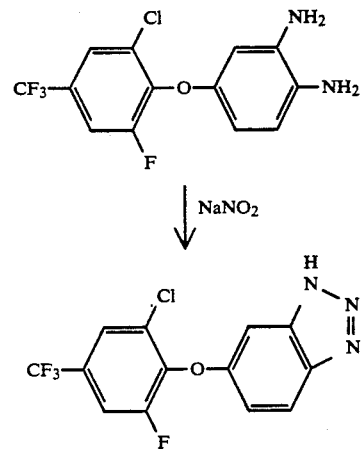

A mixture of 13.2 g of 3-chloro-5-fluoro-4-(3,4-dinitrophenoxy)benzotrifluoride, 0.3 g of 5% Pd/C and 150 mL of ethanol is shaken in a Parr hydrogenation apparatus under 50 psi of $H_2$. During the course of the reaction, 0.8 g of 5% Pd/C is added in 2 portions over a 5 hour period. After a total of 23 hours, when the uptake of $H_2$ appears to cease, the reaction is filtered and concentrated in vacuo to give a residue. This residue is dissolved in 100 mL of acetic acid and added, slowly over 3 hours, to a solution of 2.64 g of $NaNO_2$ in 30 mL of water and 50 mL of acetic acid at 5° C. After stirring at 5° C. to 20° C. for an additional 1½ hours, the reaction mixture is concentrated in vacuo to afford the title product, 20.4 g.

EXAMPLE 4

Preparation of methyl 6-[(2-chloro-α,α,α-trifluoro-p-tolyl)oxy]-1H-benzotriazole-1-acetate and methyl 5-[(2-chloro-α,α,α-trifluoro-p-tolyl)oxy]-1H-benzotriazole-1-acetate

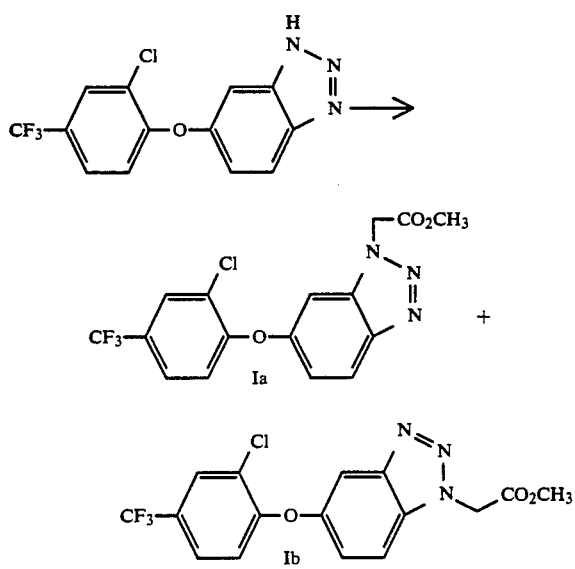

A mixture of 2.5 g of 6-(2-chloro-4-trifluoromethylphenoxy)-1H-benzotriazole, 1.59 g of methyl bromoacetate, and 2.07 g of powdered potassium carbonate in 30 mL of dimethylformamide is stirred qt room temperature for 24 hours. The mixture is concentrated in vacuo, and the resultant residue is partitioned between methylene chloride and water. The organic phase is washed with water, dried, and concentrated in vacuo, and this residue, which contains a mixture of alkylated products, is purified by HPLC using hexane-methyl-t-butyl ether as eluant to afford 0.92 g of Ia as a gum, 97.6% pure by HPLC, identified by NMR, and 0.74 g of IB as a gum, 96.2% pure by HPLC, identified by NMR.

Using essentially the same procedure, and substituting methyl-α-bromopropionate as electrophile, affords 1.05 g of methyl 6-[(2-chloro-α,α,α-trifluoro-p-tolyl)oxy]-α-methyl-1H-benzotriazole-1-acetate as a gum of 97.3% purity, identified by NMR; 1.09 g of methyl 5-[(2-chloro-α,α,α-trifluoro-p-tolyl)oxy]-α-methyl-2H-benzotriazole-1-acetate as a gum of 93.9% purity, identified by NMR; and 0.77 g of methyl 5-[(2-chloro-α,α,α-trifluoro-p-tolyl)oxy]-α-methyl-1H-benzotriazole-1-acetate as a gum of 96.0% purity, identified by NMR.

Using essentially the same procedure, and substituting methyl-α-bromopropionate and 5-(2-chloro-6-fluoro-4-trifluoromethylphenoxy)-1,2,3-benzotriazole as reactants, affords 0.87 g of methyl 6-[(2-chloro-α,α,α,6-tetrafluoro-p-tolyl)oxy]-α-methyl-1H-benzotriazole-1-acetate as a gum, identified by NMR; 1.68 g of methyl 5-[(2-chloro-α,α,α,6-tetrafluoro-p-tolyl)oxy]-α-methyl-2H-benzotriazole-1-acetate as a gum, identified by NMR; and 1.38 g of methyl 5-[(2-chloro-α,α,α,6-tetrafluoro-p-tolyl)oxy]-α-methyl-1H-benzotriazole-1-acetate as a gum, identified by NMR.

EXAMPLE 5

Preparation of 3-{5-[2-chloro-α,α,α-trifluoro-p-tolyl)oxy]-2-nitroanilino}propionitrile

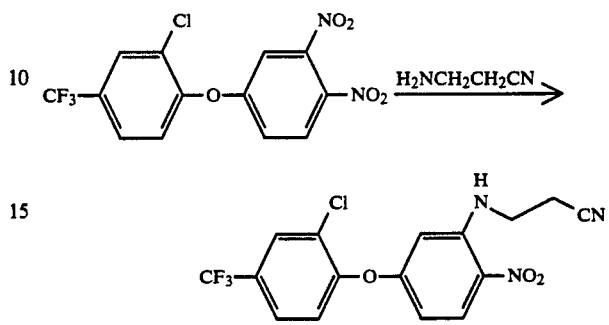

A solution of 2.8 g of 3-chloro-4-(3,4-dinitrophenoxy)benzotrifluoride and 1.09 g of β-aminopropionitrile in 10 mL acetonitrile is heated at reflux temperature for 8 hours. The solution is concentrated in vacuo, and the residue is dissolved in methylene chloride, washed twice with water, and concentrated in vacuo to give solid residue. Recrystallization from methanol affords the title compound, 3.08 g HPLC indicates 95.7% purity, mass spectral analysis indicates MW 385.

Using essentially the same procedure and substituting 3-chloro-5-fluoro-4-(3,4-dinitrophenoxy)benzotrifluoride and the appropriate amino alcohol, amino aldehyde, dimethylacetal or amino acid, the following compounds are obtained.

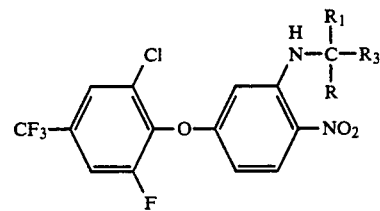

| R | R₁ | R₃ |
|---|---|---|
| CH₃ | H | CH₂OH |
| CH₃ | CH₃ | CH₂OH |
| C₆H₅ (R-isomer) | H | CH₂OH |
| C₆H₅ (S-isomer) | H | CH₂OH |
| CH₃ | H | CH(OCH₃)₂ |
| CH₃ | H | CH₂COOH |

EXAMPLE 6

Preparation of 3-{6-[(2-chloro-α,α,α-trifluoro-p-tolyl)oxy]}propionitrile

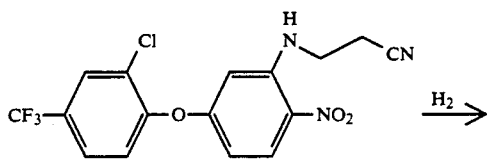

-continued

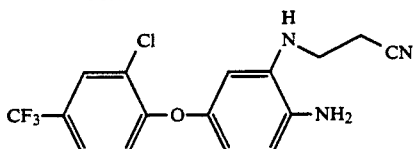

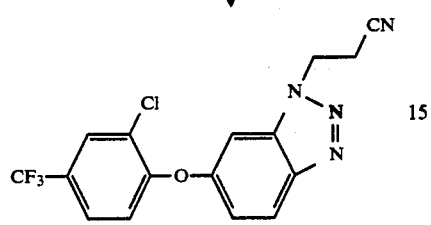

A solution of 3.0 g of 3-chloro-4-(3-β-cyanoethylamino-4-nitrophenoxy)benzotrifluoride in 100 mL absolute methanol containing 0.3 g of 5% Pd/C is shaken in a Parr hydrogenation apparatus, initially at 40 psi H₂, for 5 hours. The resulting mixture is filtered and concentrated in vacuo to afford the crude diamine, identified by mass spectral analysis.

This material is dissolved in 40 mL acetic acid, cooled to 5° C., and 0.59 g NaNO₂ dissolved in 5 mL water is added over 4 minutes. The resulting mixture is stirred at room temperature for 1 hour and concentrated in vacuo to give a residue. The residue is dissolved in methylene chloride, washed sequentially with aqueous Na₂CO₃ ad water, dried and concentrated in vacuo to afford the title product 2.45 g, as a gum: HPLC analysis indicates 92.8% purity; the product is further identified by mass spectral analysis (MW 366).

Using essentially the same procedure and employing the appropriate N-substituted 5-[(2-chloro-α,α,α,6-tetrafluoro-p-tolyl)oxy]-2nitroaniline compound as starting material, the following compounds are obtained.

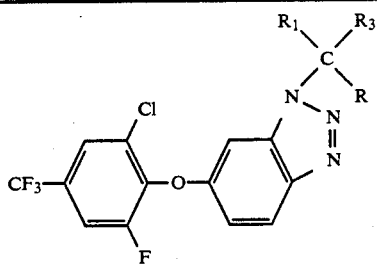

| R | R₁ | R₃ | mp °C. |
|---|---|---|---|
| CH₃ | H | CH₂OH | gum |
| CH₃ | CH₃ | CH₂OH | 132–134 |
| C₆H₅ (R-isomer) | H | CH₂OH | 85–86 |
| C₆H₅ (S-isomer) | H | CH₂OH | 83–84 |
| CH₃ | H | CH(OCH₃)₂ | 90–97.5 |
| CH₃ | H | CH₂COOH | 212–215 |

The above compounds are identified by NMR and elemental analyses.

EXAMPLE 7

Preparation of 2-aminopropionaldehyde dimethyl acetal

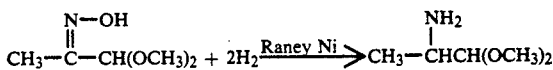

A mixture of pyruvic aldehyde dimethyl acetal oxime (38 g) and Raney nickel (5.63 g) in methanol is shaken in a Parr hydrogenator under 17–54 psig hydrogen. An additional 5.5 g of Raney nickel is added as needed and hydrogenation at 27–45 psig is continued until about 90% of the theoretical quantity of hydrogen is absorbed. The reaction mixture is filtered, and the filtrate is concentrated by distillation through a 30-cm column. When the distillate boiling point reaches 78° C., 75 ml of absolute ethanol is added and distillation is continued to give a 26 g (78%) fraction boiling at 138°–140° C. A twice-distilled sample of the title compound, bp 90°–100° C. (145 mm), is identified by elemental and NMR analyses.

EXAMPLE 8

Preparation of benzyl 3-chloro-4-nitrophenyl ether

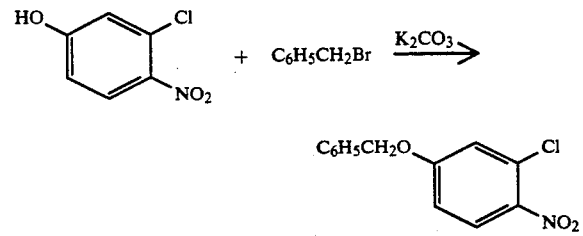

A mixture of 3-chloro-4-nitrophenol (10 g, 0.058 mole), benzyl bromide (11.8 g, 0.069 mole), and potassium carbonate (16 g, 0.116 mole) in acetone is stirred, heated at reflux temperature for 17 hours, cooled and filtered. The filtrate is concentrated in vacuo to give a solid residue which is recrystallized from absolute ethanol to give the title compound, mp 82°–84.5° C., identified by elemental and NMR analyses.

EXAMPLE 9

Preparation of 2-[5-(benzyloxy)-2-nitroanilino]-propionaldehyde dimethyl acetal

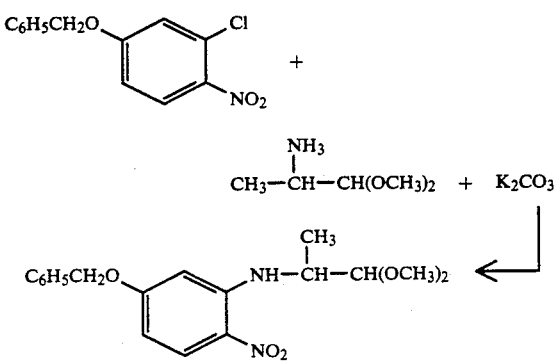

A mixture of benzyl 3-chloro-4-nitrophenyl ether (48.2 g, 0.183 mole), 2-aminopropionaldehyde dimethyl acetal (65.3 g, 0.55 mole), potassium carbonate (101 g, 0.73 mole) and toluene in dry dimethyl sulfoxide, under nitrogen, is stirred at 99°–105° C. for 20 hours, cooled to room temperature and filtered. The filter cake is washed with ether. The combined filtrates are mixed with ice water. The phases are separated and the aqueous phase is extracted with ether. The ether extracts are combined with the organic phase. The combined organic phase is washed with six portions of water, dried (Na2SO4) and concentrated in vacuo to give an oil residue which is crystallized in methanol to afford the title product as a yellow solid, 39.6 g (64.5%). A sample is recrystallized from methanol to afford a yellow solid, mp 57°–62° C., identified by elemental and NMR analyses.

EXAMPLE 10

Preparation of 2-[2-amino-5-(benzyloxy)anilino]propionaldehyde dimethyl acetal

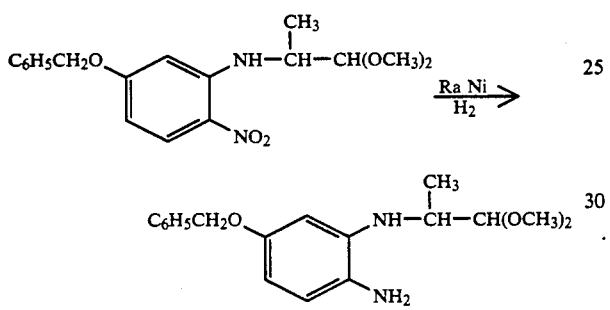

A solution of 2-[5-(benzyloxy)-2-nitroanilino]propionaldehyde dimethyl acetal (24.0 g, 0.0715 mole) in tetrahydrofuran is treated with Raney nickel (10 g) and placed in a Parr shaker hydrogenation apparatus under 20.5–37 psig hydrogen at ambient temperature. After the uptake of the theoretical quantity of hydrogen, the mixture is filtered and the filtrate is concentrated in vacuo to afford the title product as a dark-colored syrup. The product is identified by infrared and mass spectral analyses.

EXAMPLE 11

Preparation of 6-(benzyloxy)-α-methyl-1H-benzotriazole-1-acetaldehyde dimethyl acetal

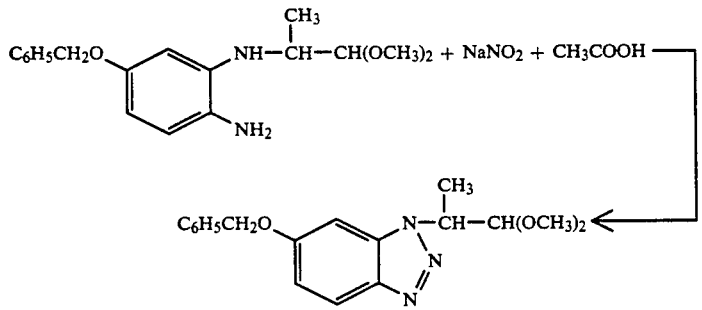

A solution of NaNO2 (34 g, 0.492 mole) in water is added to a cold (3° C.) solution of acetic acid and water. A cold (4° C.) solution of 2-[2-amino-5-(benzyloxy)anilino]-propionaldehyde dimethyl acetal in dimethoxyethane is then added in one portion to the vigorously-stirred NaNO2 acetic acid solution. The reaction temperature rises to 22° C. The reaction mixture is stirred at 18°–22° C. for 20 minutes, cooled to 5° C., and filtered. The solid filter cake is washed with water and dried at 50° C., to give the title product as a white solid, 75.7 g (65.7%). A sample is recrystallized twice from 1:1 toluene-heptane solution to a white solid, mp 101°–103° C. (sinter 100° C.), identified by elemental and NMR analyses.

EXAMPLE 12

Preparation of 6-(benzyloxy)-α-methyl-1H-benzotriazole-1-acetic acid

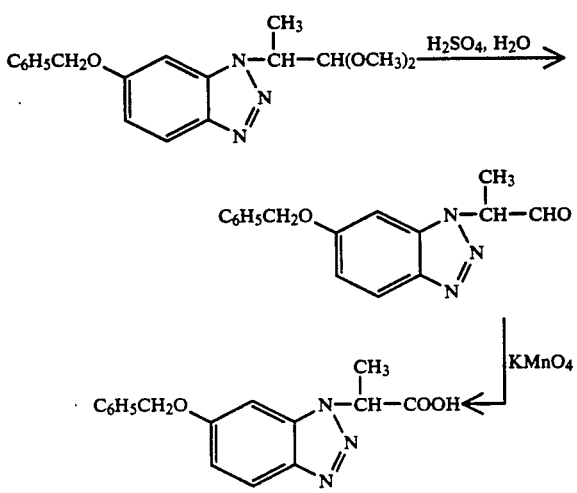

A solution of 6-(benzyloxy)-α-methyl-1H-benzotriazole-1-acetaldehyde dimethyl acetal (95 g, 0.272 mole) and concentrated sulfuric acid (20 ml) in acetic acid and water is heated at 72° C. for 20 hours, cooled to room temperature and concentrated in vacuo. The concentrated solution is diluted with acetone and water and treated with KMnO4 (140 g) in portions over a three hour period at 18°–30° C. with stirring.

The reaction mixture is decanted and filtered. The filtrate is concentrated in vacuo to remove acetone, diluted with water, cooled in an ice bath, and the resulting precipitate is removed by filtration to give the title product. A sample of this solid is recrystallized twice from aqueous ethanol to afford a white solid, mp 213°–215° C., identified by elemental and NMR analyses.

EXAMPLE 13

Preparation of methyl
6-(benzyloxy)-α-methyl-1H-benzotriazole-1-acetate

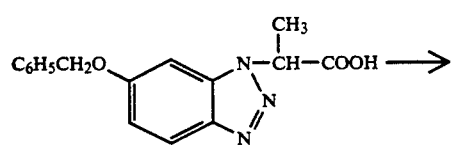

A mixture of 6-(benzyloxy)-α-methyl-1H-benzotriazole-1-acetic acid (36.6 g, 0.123 mole) and concentrated sulfuric acid (2.7 ml) in methanol is stirred at reflux temperature for 6 hours, cooled in an ice bath and treated with $K_2CO_3$ (25 g). The resulting mixture is stirred vigorously until a thick slurry results, diluted with methylene chloride and filtered. The filtrate is concentrated in vacuo to give a solid residue. Recrystallization of the residue from methanol affords the title product as a white solid, 27 g, mp 88°–91.5° C., identified by NMR and elemental analyses. Another 4.2 g (81.7% total yield) of the title product is obtained form the mother liquor.

EXAMPLE 14

Preparation of methyl
6-hydroxy-α-methyl-1H-benzotriazole-1-acetate

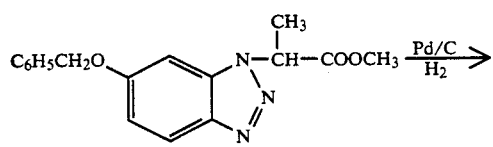

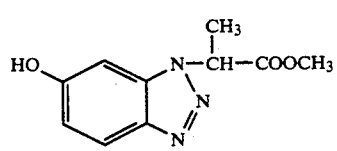

A solution of methyl 6-(benzyloxy)-α-methyl-1H-benzotriazole-1-acetate (31 g, 0.1 mole) in dimethoxyethane and methanol is shaken with 10% palladium on carbon catalyst (8 g, 50% water wet) under 24–33 psig of hydrogen in a Parr apparatus until approximately 0.1 mole of $H_2$ is absorbed (2½ hours). The reaction mixture is filtered and the filtrate is concentrated in vacuo to give the title compound as an off-white solid, 21.7 g, mp 132.5°–134.5° C., identified by NMR and elemental analyses.

EXAMPLE 15

Preparation of methyl
α-methyl-6-[(2-nitro-α,α,α-trifluoro-p-tolyl)oxy]-1H-benzotriazole-1-acetate

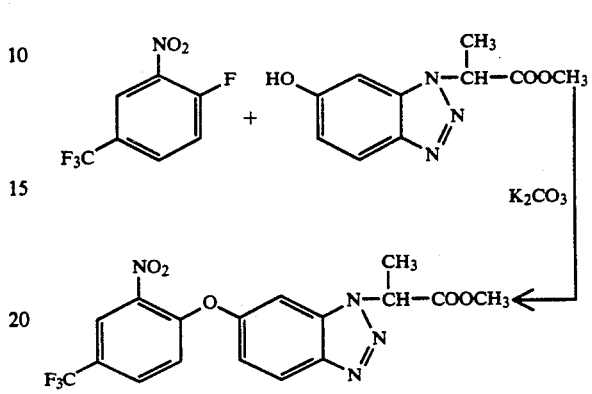

A mixture of methyl 6-hydroxy-α-methyl-1H-benzotriazole-1-acetate (2.21 g, 0.01 mole), 4-fluoro-3-nitrobenzotrifluoride (2.09 g, 0.01 mole), and $K_2CO_3$ (5.5 g, 0.04 mole) in dry dimethyl sulfoxide is stirred at 22° C. for 16 hours, diluted with chloroform and filtered. The filtrate is washed with two portions of water and two portions of saturated aqueous NaCl, dried over $Na_2SO_4$ and concentrated in vacuo to give a gum residue. The residue is crystallized from 60% aqueous ethanol to give 3.8 g of the title product as a yellow solid. A sample is recrystallized twice from 80% aqueous ethanol to give a yellow solid, mp 84.5°–88.2° C., identified by elemental and NMR analyses.

Using essentially the same procedure and substituting the appropriate haloaryl starting material, the following compounds are obtained.

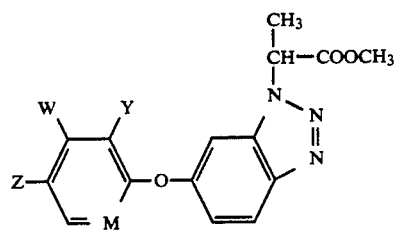

| M | W | Y | Z | mp °C. |
|---|---|---|---|---|
| C—NO$_2$ | Cl | H | CF$_3$ | 107–112 |
| C—NO$_2$ | H | NO$_2$ | CF$_3$ | 113–122 |
| N | H | H | CF$_3$ | gum |
| N | H | Cl | Cl | gum |
| N$^+$—O$^-$ | H | H | CF$_3$ | — |
| N$^+$—O$^-$ | H | Cl | Cl | — |

EXAMPLE 16

Preparation of
6-[(2-chloro-α,α,α,6-tetrafluoro-p-tolyl)oxy]-α-methyl-
1H-benzotriazole-1-acetic acid

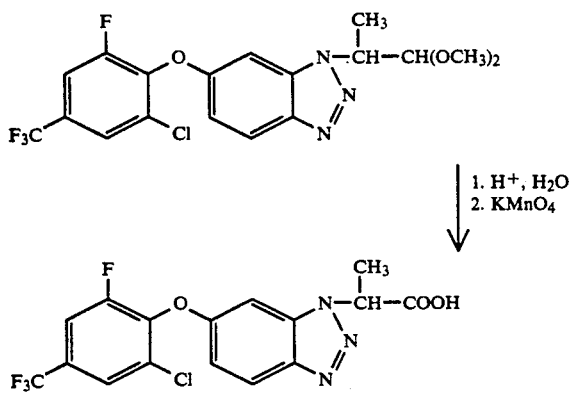

A solution of 6-[(2-chloro-α,α,α,6-tetrafluoro-p-tolyl)oxy]-α-methyl-1H-benzotriazole-1-acetaldehyde dimethyl acetal (23.0 g, 0.053 mole) in acetic acid is treated with 54 mol of 2.5 N $H_2SO_4$ and heated at 70° C. for 12 hours. A portion of the reaction solution is concentrated, diluted with acetone and treated portionwise, at 25°-30° C., with an aqueous solution of $KMnO_4$ (23.7 g, 0.15 mole). Addition is continued until a persistent pink color is obtained at 27° C. The reaction mixture is filtered to remove $MnO_2$ and the filtrate is concentrated in vacuo to give a residue. Addition of water to the thus-obtained residue precipitates the title compound as a pale yellow solid, 16.6 g. A sample is recrystallized twice from 75% aqueous ethanol to afford a crystalline solid, mp 174°-175.5° C., identified by elemental and NMR analyses.

EXAMPLE 17

Preparation of
6-[(2-chloro-α,α,α,6-tetrafluoro-p-tolyl)oxy]-α-methyl-
1H-benzotriazole-1-acetic acid compound with
isopropylamine (1:1)

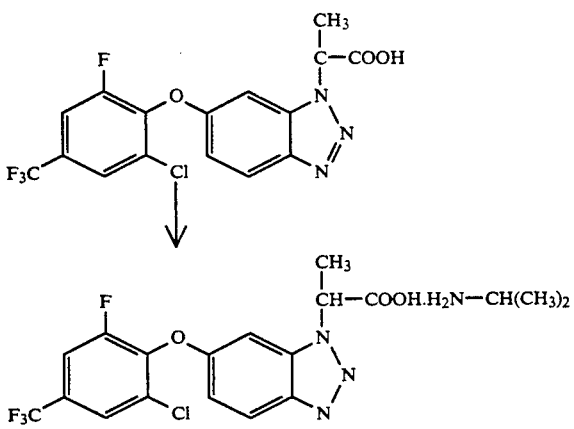

Isopropylamine (0.5 g, 0.0085 mole) is added to a solution of 6-[(2-chloro-α,α,α,6-tetrafluoro-p-tolyl)oxy]-α-methyl-1H-benzotriazole-1-acetic acid (2.0 g, 0.005 mole) in methylene chloride and the resultant solution is concentrated in vacuo to afford a gum which is dissolved in toluene. The toluene solution is concentrated to afford the title compound as a white solid, mp 103.5°-105.5°, identified by elemental and NMR analyses.

EXAMPLE 18

Preparation of methyl
6-[(2-chloro-α,α,α,6-tetrafluoro-p-tolyl)oxy]-α,α-
dimethyl-1H-benzotriazole-1-acetate

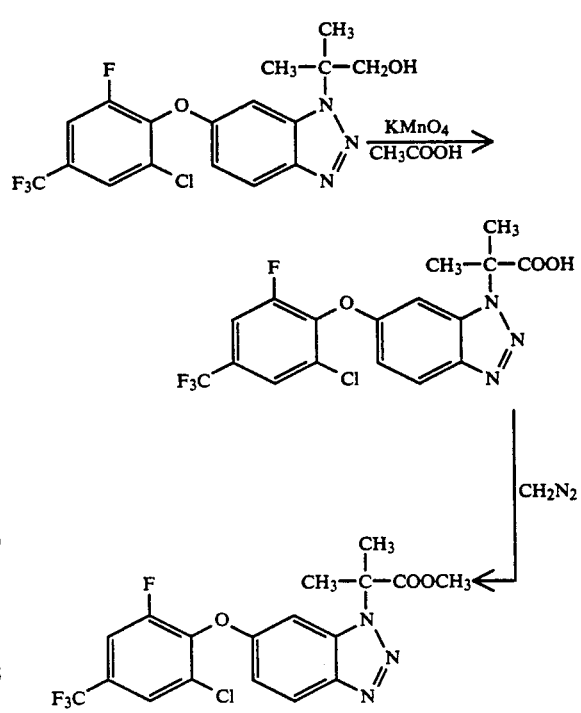

A solution of 6-[(2-chloro-α,α,α,6-tetrafluoro-p-tolyl)oxy]-α,α-dimethyl-1H-benzotriazole-1-ethanol (2.2 g, 0.00545 mole) in acetic acid and water is stirred at 56°-80° C., treated portionwise with solid $KMnO_4$ (8.5 g, 0.054 mole) over a 3 hour period, cooled and filtered. The filtrate is concentrated in vacuo to give a gum residue. The residue is chromatographed on silica gel with 15% tetrahydrofuran in chloroform to afford a white solid, 1.2 g. The solid is dissolved in methanol, treated with a solution of diazomethane in tetrahydrofuran, heated on a steam bath and concentrated in vacuo to give a solid residue. Chromatography of the residue using silica gel and 5% tetrahydrofuran in carbon tetrachloride as eluant affords the title product as a white solid, 0.65 g, mp 76.8°-80° C., identified by elemental and NMR analyses.

EXAMPLE 19

Preparation of
6-[(2-chloro-α,α,α,6-tetrafluoro-p-tolyl)oxy]-α-methyl-
1H-benzotriazle-1-acetaldehyde

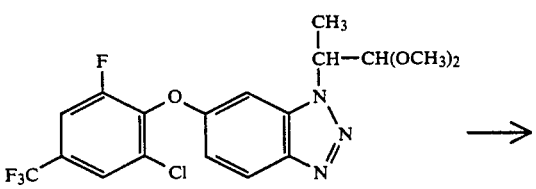

-continued

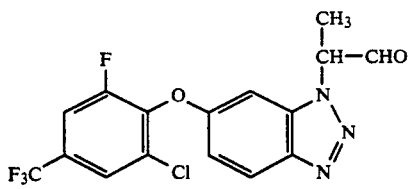

A solution of 6-[(2-chloro-α, α,α,6-tetra-fluoro-p-tolyl)oxy]-α-methyl-1H-benzotriazole-1-acetaldehyde dimethyl acetal (20 g, 0.046 mole) in acetic acid is treated with 47 ml of 2.5 N $H_2SO_4$, heated for 12 hours at 70° C., cooled and diluted with water and methylene chloride. The phases are separated and the aqueous phase is extracted with methylene chloride. The combined organic phases are dried ($MgSO_4$), filtered through a pad of $Al_2O_3$, and concentrated in vacuo to afford the title compound as a solid, mp 106°–108° C., characterized by elemental and NMR analyses.

EXAMPLE 20

Preparation of 6-[(2-chloro-α,α,α,6-tetrafluoro-p-tolyl)oxy]-α-methyl-1h-benzotriazole-1-acetaldehyde oxime

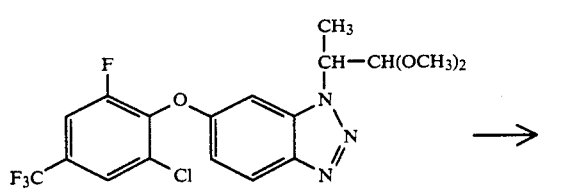

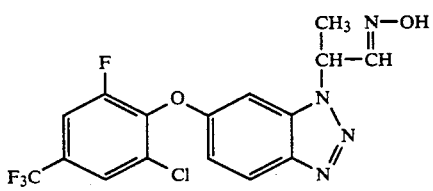

A solution of 6-[(2-chloro-α,α,α,6-tetrafluoro-p-tolyl)oxy]-α-methyl-1H-benzotriazole-1-acetaldehyde dimethyl acetal (23.0 g, 0.053 mole) in acetic acid is treated with 54 ml of 2.5N $H_2SO_4$ and stirred at 70° C. for 12 hours. A 15 ml portion of the reaction solution is diluted to a total volume of 100 ml with water, the resulting precipitate is separated, washed with water, treated with a solution of hydroxylamine hydrochloride (1.0 g, 0.014 mole) in pyridine and ethanol, heated at 85° C. for several hours, cooled and concentrated in vacuo to give a solid residue. Recrystallization from aqueous ethanol, ethanol and toluene gives the title compound mp 148°–151° C., identified by elemental and NMR analyses.

EXAMPLE 21

Preparation of 6-[(2-chloro-α,α,α,6-tetrafluoro-p-tolyl)oxy]-α-methyl-1H-benzotriazole-1-acetonitrile (I) and 6-[(2-chloro-α,α,α,6-tetrafluoro-p-tolyl)oxy]-α-methyl-1H-benzotriazole-1-acetaldehyde O-acetylaxime (II)

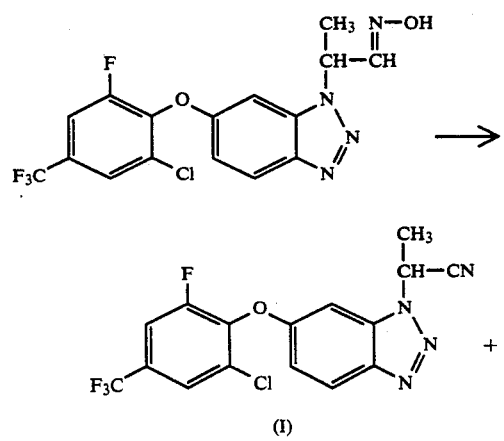

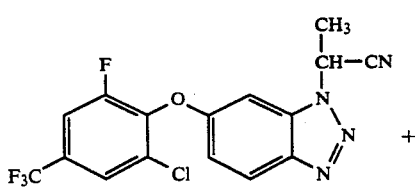

(I)

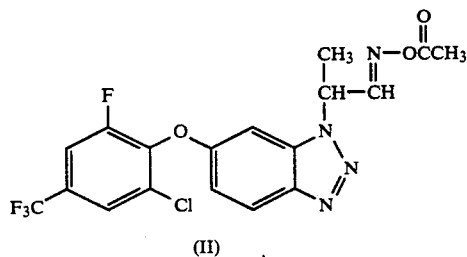

(II)

A solution of 6-[(2-chloro-α,α,α,6-tetra-fluoro-p-tolyl)oxy]-α-methyl-1H-benzotriazole-1-acetaldehyde oxime (5.0 g, 0.012 mol) in acetic anhydride is allowed to stand at 22° C. for 20 hours and concentrated in vacuo to give an oil residue. The residue is chromatographed on silica gel using chloroform as eluant to afford the title compound (I), 2.0 g, mp 118°–119° C., identified by elemental and NMR analyses and the title compound (II), 2.1 g, mp 95°–96° C., identified by elemental and NMR analyses.

EXAMPLE 22

Preparation of 6-[(2-chloro-α,α,α,6-tetrafluoro-p-tolyl)oxy]-α-methyl-1H-benzotriazole-1-acetaldehyde semicarbazone

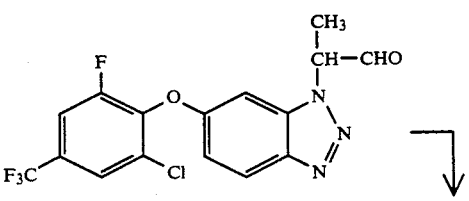

-continued

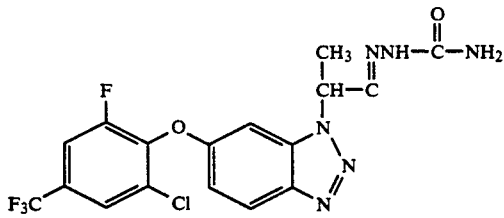

A mixture of 6-[(2-chloro-α,α,α,6-tetrafluoro-p-tolyl)oxy]-α-methyl-1H-benzotriazole-1-acetaldehyde (0.0295 mole), semicarbazide hydrochloride (4.0 g, 0.035 mole), and sodium acetate (5.8 g, 0.071 mole) in aqueous ethanol is heated to reflux temperature, cooled and filtered. The solid filter cake is recrystallized from ethanol to give the title compound as a solid, mp 170°–171° C., identified by elemental and NMR analyses.

EXAMPLE 23

Preparation of 6-[(2-chloro-α,α,α,6-tetrafluoro-p-tolyl)oxy]-α-methyl-1H-benzotriazol1-acetaldedhyde (2,4-dinitrophenyl)hydrazone

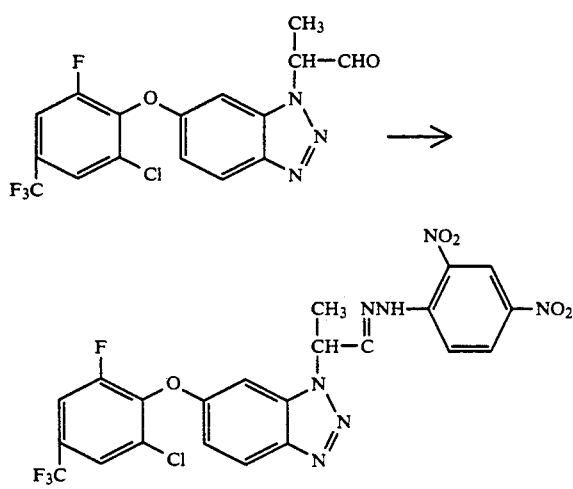

A solution of 6-[(2-chloro-α,α,α,6-tetrafluoro-p-tolyl)oxy]-α-methyl-1H-benzotriazol-1-acetaldedhyde (0.0294 mole) in ethanol is added to a solution of 2,4-dinitrophenylhydrazine (7 g, 0.035 mole) and conc. $H_2SO_4$ (35 ml, 0.63 mole) in $H_2O$ at 50° C., allowed to come to room temperature and filtered. The solid filter cake is recrystallized from aqueous acetic acid and from ethanol to afford the title compound, mp 148°–149° C., identified by elemental and NMR analyses.

EXAMPLE 24

Preparation of (S)-6[(2-chloro-α,α,α,6-tetrafluoro-p-tolyl)oxy]-α-phenyl-1H-benzotriazole-1-acetaldehyde

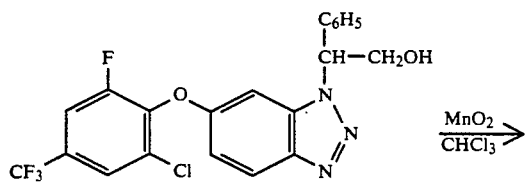

-continued

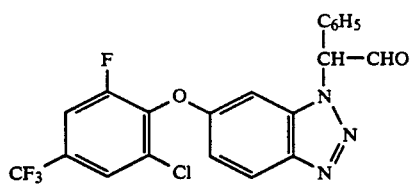

A mixture of (S)-6-[(2-chloro-α,α,α,6-tetrafluoro-p-tolyl)oxy]-β-phenyl-1H-benzotriazole-1-ethanol (1.0 g, 0.0022 mole) i chloroform is treated with $MnO_2$, (1.0 g, 0.0115 mole) stirred at 40° C. for 18 hours and filtered through a bed of diatomaceous earth. The filtrate is concentrated in vacuo to give a residue which is chromatographed using silica gel and 10% tetrahydrofuran in carbon tetrachloride to yield the title product as a white solid, 0.42 g, mp 84°–85° C., characterized by elemental and NMR analyses.

EXAMPLE 25

Preparation of 6-[(2-chloro-α,α,α,6-tetrafluoro-p-tolyl)oxy]-α-methyl-1H-benzotriazole-1-acetyl chloride

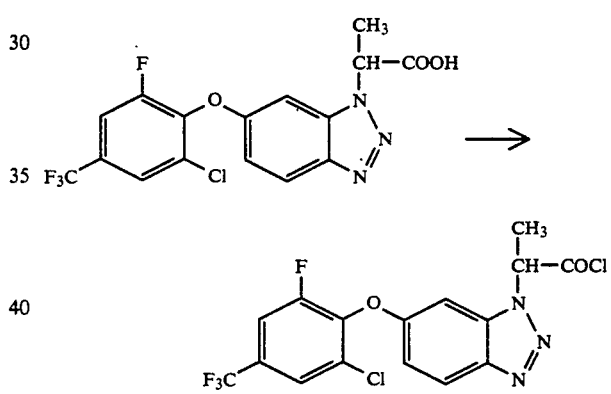

A mixture of 6-[(2-chloro-α,α,α,6-tetrafluoro-p-tolyl)oxy]-α-methyl-1H-benzotriazole-1-acetic acid (2.0 g, 0.005 mole), $SOCl_2$ (3 ml, 0.04 mole), methylene chloride and dimethylformamide (2 drops) is heated at reflux temperature for 2 hours, cooled and concentrated in vacuo to give a residue and which is chased twice with xylene at 65° C. The resultant residue is identified as the title product by infrared analysis.

EXAMPLE 26

Preparation of N-butyl-6-[(2-chloro-α,α,α,6-tetrafluoro-p-tolyl)oxy]-α-methyl-1H-benzotriazole-1-acetamide

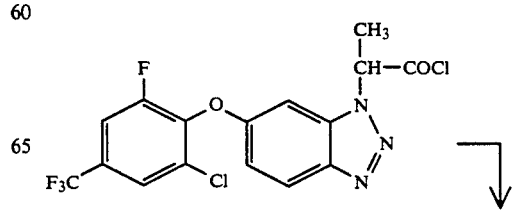

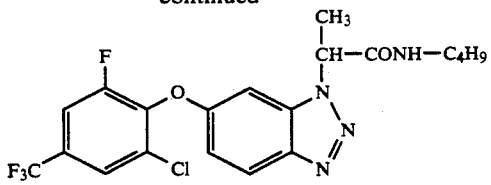

A solution of 6-[(2-chloro-α,α,α,6-tetrafluoro-p-tolyl)oxy]-α-methyl-1H-benzotriazole-1-acetyl chloride (0.0084 mole) in toluene is added to n-butylamine (1.22 g, 0.0167 mole) at 22° C., stirred for 1 hour at ambient temperature and filtered. The solid filter cake is recrystallized from aqueous ethanol to afford the title compound as a white solid, mp 142°–143° C., identified by elemental and NMR analyses.

Using essentially the same procedure and substituting the appropriate amine, the following compounds are obtained.

| $R_5$ | $R_6$ | mp °C. |
|---|---|---|
| H | H | 177–178 |
| H | $C_6H_5$ | 175.5–176 |
| $CH_3$ | $C_6H_5$ | 132–133 |
| $C_2H_5$ | $C_2H_5$ | gum |

The above compounds are identified by NMR analysis.

EXAMPLE 27

Preparation of methylallyl 6-[(2-chloro-α,α,α,6-tetrafluoro-p-tolyl)oxy]-α-methyl-1H-benzotriazole-1-acetate

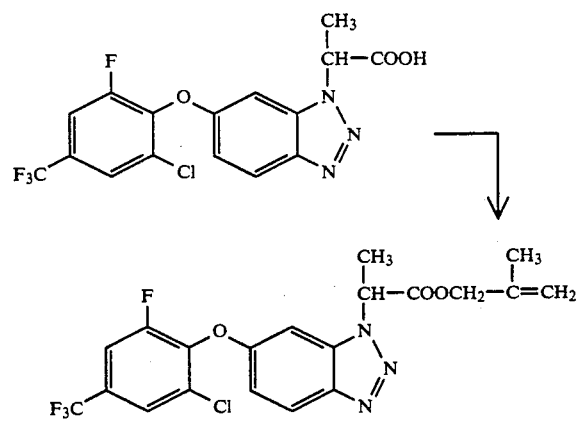

A mixture of 6-[(2-chloro-α,α,α,6-tetrafluoro-p-tolyl)oxy]-α-methyl-1H-benzotriazole-1-acetic acid, thionyl chloride (0.8 ml, 0.011 mole), and 2 drops of dimethylformamide i methylene chloride is heated at reflux temperature for 2 hours, cooled and concentrated in vacuo to give a residue which is re-evaporated four times with toluene at 60°. The resultant residue is treated with 2-methylallyl alcohol and pyridine, shaken until reaction is complete by infrared spectral analysis and concentrated in vacuo to give a residue. The thus-obtained residue is dissolved in 1T acetonitrile in carbon tetrachloride and filtered through a pad of silica. The filtrate is concentrated in vacuo to give a solid residue. The solid residue is recrystallized from warm heptane to afford the title compound as a white solid, mp 71°–74° C., identified by elemental and NMR analyses.

Using essentially the same procedure and substituting n-hexyl alcohol affords n-hexyl 6-[(2-chloro-α,α,α,6-tetrafluoro-p-tolyl)oxy]-α-methyl-1H-benzotriazole-1-acetate as a gum, characterized by elemental and NMR analyses.

EXAMPLE 28

Postemergence herbicidal evaluation of test compounds

The postemergence herbicidal activity of the compounds of the present invention is demonstrated by the following tests wherein seeds or tubers of each species are planted 6 to 21 days prior to treatment, depending on the rate of growth of the seedlings. Each species is planted in an individual container and then all species assembled into an 11×11 inch tray for treatment. Planting is times to that monocot species having 2 to 4 leaves and dicots have cotyledons plus 1 to 3 leaves at treatment. After planting, trays are watered with an overhead mis and/or sub-irrigation to maintain moisture until ready for treatment. After treatment plants are watered by sub-irrigation only during the evaluation period.

In most cases the data are for a single test, but in several instances, they are average values obtained from more than one test.

| Plant Species Used | |
|---|---|
| Velvetleaf | *Abutilon theophrasti* |
| Oats, cultivated | *Avana sativa* |
| Sicklepod | *Cassia obtusifolia* |
| Nutsedge, yellow | *Cyperus esculentus* |
| Barnyardgrass | *Echinochola crusgalli* |
| Soybeans | *Glycine max* |
| Morningglory | *Ipomea Sp.* |
| Sebania, hemp | *Sesbania exaltata* |
| Foxtail, yellow | *Setaria glauca* |
| Sida, prickley | *Sida spinosa* |
| Johnsongrass | *Sorghum halapense* |
| Corn, cultivated | *Zea mays* |
| Lambsquarters | *Chenopodium album* |
| Jimsonweed | *Datura stramonium* |

| Description of Symptoms | | | |
|---|---|---|---|
| Major Category | Rating Symbol | Subcategory | Rating Symbol |
| Desiccation of Tissue | D | a. New growth occurring | Z |
| | | b. Extreme variation in individual plant response | V |
| Inhibition | I | a. Break of axillary buds | X |
| | | b. Bleach or loss of color | B |
| | | c. Malformed seedlings | M |
| Abnormal Growth | A | a. Abnormal leaves | L |
| | | b. Twisting and bending of stems | T |
| | | c. Elongation of internodes | E |
| | | d. Rosetting or Shortening | R |
| Color Change | C | a. Loss of green color with yellow appearing tissue | Y |
| | | b. Loss of green color with white appearing tissue | W |
| | | c. Increased red or pink pigments with or with- | P |

| Description of Symptoms | | |
|---|---|---|
| Major Category | Rating Symbol Subcategory | Rating Symbol |
| | -continued out loss of green | |

| Severity of Injury | | |
|---|---|---|
| Rating Scale | Category of Injury | |
| 10 | No regenerative tissue present | Death |
| 9 | No leaves expanded | Severe Injury |
| 8 | Leaves smaller than cotyledons or <1 inch | Severe Injury |
| 7 | Leaves larger than cotyledons or >1 inch | Severe Injury |
| 6 | Normal growth would not be expected | Moderate Injury |
| 5 | Normal growth would not be expected | Moderate Injury |
| 4 | Normal growth would not be expected | Moderate Injury |
| 3 | Temporary (maximum acceptable for crops) | Slight Injury |
| 2 | Superficial (obvious but no stunting) | Slight Injury |
| 1 | Minimum apparent injury | Slight Injury |
| 0 | Not different from untreated reference | No effect |

The potting media for postemergence testing was either TERRA-LITE ®, Metro-Mix 300, 300, from W. R. Grace & Co., Cambridge, Mass., containing peat moss, vermiculite, perlite, composted pine bark, granite sand, and a wetting agent or a custom blend of natural silt loam soil:HYPONEX ® top soil: perlite, 1:1:8 (v/v/v), plus 20-20-20 soluble fertilizer equivalent to 1,121 kg/ha.

The test compounds of the invention are dissolved in a solvent system of acetone:methanol:dimethylformamide, 90:8:2 (v/v/v) and the solution is atomized onto the plants at a rate equivalent to 561 L per hectare. Atomizing is accomplished by using air pressure to force the solution through a standard even-fan agricultural spray nozzle. Rate of application is controlled by placing the experimental units on a constant speed belt which carries them under the spray nozzle. After spraying, the plants are placed on greenhouse benches and are cared for in the usual manner commensurate with conventional greenhouse practices. From 1 to 3 weeks after treatment the seedling plants ar examined and rated according to the rating system provided below. The data obtained are recorded in table I below.

TABLE I

Postemergence Tests- Rates in Kg/ha

| Compound | Rate | Prick sida | Jimso nweed | Sickl epod | Lambs quart | Sesb ania | Velve tleaf | Morni nggly | Nuts edge |
|---|---|---|---|---|---|---|---|---|---|
| Methyl 6-[(2-chloro-alpha,alpha,alpha-trifluoro-p-tolyl)oxy]-alpha-methyl-1H-benzotriazole-1-acetate | 5.6040 | 10D | 10D | 10D | 8D | 10D | 10D | — | 9D |
| | 1.1210 | 10D | 9D | 9D | 10D | 10D | 10D | 8IM | 1D |
| | 0.5604 | 10D | 10D | 10D | 10D | 10D | 10D | 10D | 3D |
| | 0.1121 | 10D | 10D | 9DZ | 10D | 10D | 7ID | 10D | 2D |
| | 0.0560 | 10D | 10D | 10D | 10D | 10D | 10D | 10D | 3D |
| | 0.0112 | 9D | 10D | 10D | 10D | 9D | 9DZ | 10D | 2DAL |
| | 0.0056 | 7D | 10D | 10D | 10D | 8D | 10D | 10D | 0 |
| | 0.0011 | 2IAL | 5IM | 5DALZ | 10D | 3I | 1I | 4IALM | — |
| | 0.0005 | 2AL | 3I | 2AL | — | 2I | 2AL | 3AL | 0 |
| | 0.0001 | 1AL | 1I | 1AL | — | 0 | 1AL | 2AL | 0 |
| Methyl 6-[(2-chloro-alpha,alpha,alpha,6-tetrafluoro-p-tolyl)oxy]-alpha-methyl-1H-benzo-triazole-1-acetate | 1.1210 | 10D | — | 10D | — | 10D | 10D | 10D | 10D |
| | 0.1121 | 10D | — | 10D | — | 10D | 10D | 10D | 3D |
| | 0.0112 | 10D | — | 10D | — | 10D | 10D | 10D | 1D |
| Methyl 6[(2-chloro-alpha,alpha,alpha-trifluoro-p-tolyl)-oxy]-1H-benzotriazole-1-acetate | 1.2100 | 10D | 10D | 9D | 10D | 9D | 9D | 10D | 8D |
| | 1.1210 | 9D | 10D | 9DI | 10D | 9D | 9D | 10D | 2D |
| | 0.5604 | 5DIM | 10D | 8DIZ | 10D | 9D | 7DI | 10D | 1D |
| | 0.1121 | 6DIM | 10D | 7DI | 10D | 9D | 5DI | 10D | 2D |
| | 0.0560 | 5I | 10D | 10D | 10D | 8D | 5I | 10D | 1D |
| | 0.0112 | 3I | 9D | — | 5I | 7I | 5I | 10D | 1I |
| Methyl 5-[(2-chloro-alpha,alpha,alpha,6-tetrafluoro-p-tolyl)oxy]-alpha-methyl-2H-benzo-triazole-1-acetate | 5.6040 | 10D | — | 8IM | — | 10D | 10D | 10D | 2CY |
| | 2,2416 | 10D | — | 7IM | — | 10D | 10D | 10D | 0 |
| | 1.1210 | 10D | — | 9DIM | — | 10D | 10D | 10D | 2ICY |
| | 0.1121 | 10D | — | 5I | — | 10D | 10D | 10D | 1I |
| | 0.0112 | 5AL | — | 0 | — | 5I | 3I | 1D | 1I |
| Methyl 5-[(2-chloro-alpha,alpha,alpha-trifluoro-p-tolyl)oxy]-alpha-methyl-2H-benzotriazole-1-acetate | 5.6040 | 9DIM | 10D | 6I | 9DI | 10D | 10D | 10D | 2DI |
| | 2.2416 | 8IM | 9D | 3I | 9D | 8DZ | 9DZ | 10D | 2I |
| | 1.1210 | 8IM | 10D | 3D | 8DIM | 8DZ | 6D | 10D | 1D |
| | 0.5604 | 8D | 9D | 0I | 5I | 8DZ | 7D | 9D | 0 |
| | 0.1121 | 5I | 9DIM | 2AL | 3DI | 5I | 5IDZ | 9DIM | 0 |
| | 0.0560 | 2I | 5IM | 1I | 3I | 3I | 5DZ | 5AL | 0 |
| | 0.0112 | 3AL | 2AL | 0 | 0 | 2I | 3AL | 5AL | — |
| Methyl 5-[(2-chloro-alpha,alpha,alpha, | 1.1210 | 10D | — | 10D | — | 10D | 10D | 10D | 0 |
| | 0.5604 | 10D | — | 10D | — | 10D | 10D | 8IM | 0 |
| | 0.1121 | 3AL | — | 3D | — | 7D | 7D | 1AL | 0 |

TABLE I-continued

Postemergence Tests- Rates in Kg/ha

| | | | | | | | | | |
|---|---|---|---|---|---|---|---|---|---|
| alpha,6-tetra-fluoro-p-tolyl)-oxy]-alpha-methyl 1H-benzotriazole-1-acetate | | | | | | | | | |
| Methyl 5-[(2-chloro-alpha, alpha,alpha-tri-fluoro-p-tolyl)-oxy]-alpha-methyl-1H-benzotriazole-1-acetate | 5.6040<br>1.1210<br>0.5604<br>0.1121 | 8IM<br>81M<br>71M<br>3I | 10D<br>81M<br>81M<br>71M | 10D<br>2I<br>3I<br>7I | 7D<br>10D<br>7D<br>5I | 10D<br>7D<br>7I<br>3AL | 9D<br>5I<br>5I<br>3AL | —<br>10D<br>7I<br>5I | 2I<br>1I<br>2I<br>0 |
| Methyl 5-[(2-chloro-alpha, alpha,alpha-tri-fluoro-p-tolyl)-oxy]-1H-benzo-triazole-1-acetate | 11.2084<br>0.1121<br>0.0560<br>0.0112 | 7D<br>0<br>1I<br>0 | 10D<br>3AL<br>2AL<br>1AL | 7IX<br>3I<br>5I<br>1I | 10D<br>2AL<br>2I<br>1I | 9D1<br>4I<br>2I<br>1I | 5DAL<br>2AL<br>2D<br>3I | 10D<br>8I<br>2I<br>1AL | 0<br>0<br>0<br>0 |

| Compound | Fox tail | Jhnsn grass | Oats | Barny ardgr | Corn | Soy beans |
|---|---|---|---|---|---|---|
| Methyl 6-[(2-chloro-alpha, alpha,alpha-trifluoro-p-tolyl)oxy]-alpha-methyl-1H-benzotria-zole-1-acetate | 10D<br>10D<br>10D<br>10D<br>10D<br>6D<br>7I<br>2I<br>1D<br>0 | 9D<br>9D<br>9D<br>8D<br>7D<br>6ID<br>5D<br>2I<br>1I<br>2I | 9D<br>9D<br>9D<br>6D<br>5D<br>2D<br>2I<br>1ID<br>0<br>0 | 9D<br>10D<br>10D<br>9D<br>7D<br>51D<br>3I<br>3ICY<br>0<br>0 | 10D<br>9D<br>10D<br>10D<br>10D<br>10D<br>10D<br>5IM<br>3I<br>1I | 8D<br>10D<br>10D<br>10D<br>10D<br>10D<br>10D<br>10D<br>—<br>— |
| Methyl 6-[(2-chloro-alpha, alpha,alpha,6-tetrafluoro-p-tolyl)oxy]-alpha-methyl-1H-benzo-triazole-1-acetate | 10D<br>10D<br>7D | 10D<br>9D<br>3D | 10D<br>10D<br>3I | 10D<br>10D<br>5D | 10D<br>8D<br>1D | 10D<br>8DZ<br>3D |
| Methyl 6[(2-chloro-alpha, alpha,alpha-tri-fluoro,p-tolyl)-oxy]-1H-benzo-triazole-1-acetate | 10D<br>7D<br>7D<br>6DI<br>7I<br>5I | 10D<br>7D<br>5D<br>4DIM<br>8D<br>5I | 5DIM<br>2D<br>2D<br>3DAL<br>2I<br>0 | 10D<br>6D<br>5D<br>4DI<br>4I<br>3I | —<br>—<br>—<br>—<br>—<br>— | —<br>—<br>—<br>—<br>—<br>— |
| Methyl 5-[(2-chloro-alpha, alpha,alpha,6-tetrafluoro-p-tolyl)oxy]-alpha-methyl-2H-benzo-triazole-1-acetate | 10D<br>10D<br>9D<br>2D<br>3I | 10D<br>10D<br>10D<br>3D<br>1I | 10D<br>4D<br>3D<br>3D<br>0 | 10D<br>10D<br>9D<br>3D<br>0 | 5D<br>1CY<br>2CY<br>2D<br>0 | 10D<br>7IM<br>5DIM<br>2AL<br>1AL |
| Methyl 5-[(2-chloro-alpha, alpha,alpha-tri-fluoro-p-tolyl)-oxy]-alpha-methyl-2H-benzotriazole-1-acetate | 9D<br>10D<br>9D<br>9D<br>6DI<br>6I<br>4I | 9D<br>9D<br>8D<br>7D<br>4DI<br>2I<br>5I | 7D<br>3D<br>5D<br>2D<br>1D<br>1CY<br>1CY | 9D<br>10D<br>10D<br>10D<br>5D<br>2CY<br>0 | —<br>—<br>—<br>—<br>—<br>—<br>— | —<br>—<br>—<br>—<br>—<br>—<br>— |
| Methyl5-[(2-chloro-alpha, alpha,alpha, alpha,6-tetra-fluoro-p-tolyl)-oxy]-alpha-methyl 1H-benzotriazole-1-acetate | 8D<br>7D<br>2D | 8D<br>3D<br>1D | 5D<br>2D<br>1D | 8D<br>5D<br>1D | 0<br>0<br>0 | 3AL<br>2AT<br>2AL |
| Methyl 5-[(2-chloro-alpha, alpha,alpha-tri-fluoro-p-tolyl)-oxy]-alpha-methyl-1H-benzotriazole-1-acetate | 71M<br>3D<br>2D<br>1I | 8D<br>5I<br>3I<br>0 | 3D<br>2I<br>2I<br>1I | 7D<br>5I<br>5I<br>2CY | —<br>—<br>—<br>— | —<br>—<br>—<br>— |
| Methyl 5-[(2-chloro-alpha, alpha,alpha-tri-fluoro-p-tolyl)-oxy]-1H-benzo- | 5D<br>0<br>0<br>0 | 4D<br>0<br>2CP<br>0 | 3D<br>0<br>0<br>0 | 4DI<br>0<br>1I<br>1D | —<br>—<br>—<br>— | —<br>—<br>—<br>— |

TABLE I-continued

| Postemergence Tests- Rates in Kg/ha |
|---|
| triazole-1-acetate |

EXAMPLE 29

Preemergence herbicidal evaluation of test compounds

The preemergence herbicidal activity of the compounds of the present invention is exemplified by the following tests in which the seeds or tubers are pressed into the surface of the potting media in individual sections of an 11×11 inch tray, then covered with approximately 0.25 inch of coarse sand. A solution of the test compound in acetone:methanol:dimethylformamide, 90:8:2 (v/v/v) is sprayed onto the sand surface at a rate equivalent to 561 L per hectare in the manner described above for postemergence testing, then approximately 0.5 inch of water is added to leach the test compound into contact with the seeds, or tubers, and into the potting media. The potting media for preemergence testing was either a blend consisting of 3 parts (by volume) of pasteurized silt loam top soil (ca. 1.5% O. M.) and one part coarse sand or the same as that described for postemergence testing above. The treated trays are placed on greenhouse benches and cared for in accordance with conventional greenhouse procedures. From 2 to 3 weeks after treatment, the trays are examined and rated according to the rating scale system set forth above. The herbicidal prociency of the active ingredients of the present invention is evident form the test results which are recorded in Table II below. When more than one test is involved for a given compound, the data are averaged.

TABLE II

| | Preemergence Tests- Rtes in Kg/ha | | | | | | | | |
|---|---|---|---|---|---|---|---|---|---|
| Compound | Rate | Prick sida | Jimso nweed | Sickl epod | Lambs quart | Sesb ania | Velve tleaf | Morni nggly | Nuts edge |
| Methyl 6-[(2-chloro-alpha,alpha,alpha-trifluoro-p-tolyl)-oxy]-alpha-methyl-1H-benzotriazole-1-acetate | 5.6040 | 10D | 10D | 10D | 10I | 10D | 10D | 10D | 10D |
| | 1.1210 | 10I | 10D | 9D | 10I | 10D | 71M | 81M | 9D |
| | 0.5604 | 5AL | 10D | 10D | 9I | 10D | 7DZ | 81M | 61M |
| | 0.1121 | 4AIL | 71M | 2D | 7I | 10D | 3AIL | 41M | 0 |
| | 0.0560 | 0 | 9I | 1D | 8I | 5I | 3I | 5AL | 0 |
| | 0.0112 | 6ICY | 5ICY | 0 | 7I | 2I | 1I | 2I | 0 |
| | 0.0056 | 1I | 1CY | 0 | 5I | 0 | 0 | 2CP | 0 |
| | 0.0011 | 0 | 0 | 0 | 2CY | 0 | 0 | 1CP | 0 |
| Methyl-6-[(2-chloro-alpha,alpha-alpha,6-tetrafluoro-p-tolyl)oxy]-alpha-methyl-1H-benzotriazole-1-acetate | 1.1210 | 10D | — | 8I | — | 10D | 10D | 10D | 10D |
| | 0.1121 | 2I | — | 3I | — | 5D | 5I | 2AL | 0 |
| | 0.0112 | 1I | — | 3I | — | 0 | 2I | 1I | 0 |
| Methyl 6-[(2-chloro-alpha,alpha,alpha-trifluoro-p-tolyl)oxy]-1H-benzotriazole-1-acetate | 11.2108 | 10I | 10I | 10D | 10I | 10D | 10D | 10D | 10D |
| Methyl 5-[(2-chloro-alpha,alpha,alpha,6-tetrafluoro-p-tolyl)oxy]-alpha-methyl-2H-benzotriazole-1-acetate | 5.6040 | 10I | — | 10D | — | 10D | 10D | 9I | 0 |
| | 2.2417 | 9DZ | — | 10D | — | 10D | 10D | 7IM | 0 |
| | 1.1208 | 7D | — | 5I | — | 5I | 7I | 3AL | 0 |
| Methyl 5-[(2-chloro-alpha,alpha,alpha-trifluoro-p-tolyl)oxy]-alpha-methyl-2H-benzotriazole-1-acetate | 5.6040 | 8IM | 10DI | 1I | 10I | 8DIM | 6IM | 7IM | 1I |
| | 2.2417 | 5IM | 9D | 0 | 10I | 7I | 3I | 2I | 0 |
| | 1.1208 | 4IM | 6IM | 0 | 6I | 5I | 1I | 2ICP | 0 |
| | 0.5604 | 5I | 2AL | 0 | 10I | 3I | 0 | 0 | 0 |
| | 0.1121 | 2I | 2AL | 0 | 10I | 1I | 0 | 1CP | — |
| Methyl 5-[(2-chloro-alpha,alpha,alpha,6-tetrafluoro-p-tolyl)oxy]-alpha-methyl-1H-benzotriazole-1-acetate | 1.1208 | 5I | — | 0 | — | 0 | 3I | 2CP | 0 |
| | 0.5604 | 2I | — | 0 | — | 0 | 3I | 0 | 2I |
| | 0.1121 | 1I | — | 1I | — | 1I | 1CY | 0 | 2I |
| Methyl 5-[(2-chloro-alpha,alpha,alpha-trifluoro-p-tolyl)-oxy]-alpha-methyl- | 5.6040 | 8IM | 91M | 8I | 9I | 9I | 8IM | 9I | 3I |
| | 1.1208 | 2I | 5AL | 0 | 8I | 1I | 1AL | 2CP | 1D |
| | 0.5604 | 0 | 5AL | 0 | 2VY | 0 | 2I | 2D | 1D |
| | 0.1121 | 0 | 2AL | 2CY | 0 | 2I | 0 | 2I | 1D |

TABLE II-continued

Preemergence Tests- Rtes in Kg/ha

| 1H-benzotriazole-1-acetate | | | | | | | | | |
|---|---|---|---|---|---|---|---|---|---|
| Methyl 5-[(2-chloro-alpha, alpha,alpha-trifluoro-p-tolyl)oxy]-1H-benzotriazole-1-acetate | 11.2084 | 4I | 10D | 7I | 10I | 3I | 6I | 4I | 3ICY |
| | 0.1121 | 7IM | 5AL | 1I | 7I | 1CY | 5IM | 0 | 0 |
| | 0.0560 | 5AL | 3AL | 0 | 7I | 0 | 3IM | 0 | 0 |
| | 0.0112 | 2AL | 2AL | 1CY | 2CY | 0 | 2I | 0 | 0 |

| Compound | Fox tail | Jhnsn grass | Oats | Barny ardgr | Corn | Soy beans |
|---|---|---|---|---|---|---|
| Methyl 6-[(2-chloro-alpha, alpha,alpha-trifluoro-p-tolyl)oxy]-alpha-methyl-1H-benzotriazole-1-acetate | 10D | 10I | 8D | 10D | 10D | 10I |
| | 10D | 10D | 3D | 10D | 10D | 10I |
| | 10D | 8D | 0 | 8D | 10D | 9I |
| | 4I | 5DI | 0 | 3ICY | 8IM | 8I |
| | 3I | 7D | 2I | 2I | 9I | 8I |
| | 1I | 4I | 0 | 2ID | 6ICY | 7I |
| | 2I | 2I | 2I | 0 | 1CY | 5I |
| | 0 | 0 | 1I | 0 | 0 | 2CY |
| Methyl-6-[(2-chloro-alpha, alpha-alpha,6-tetrafluoro-p-tolyl)oxy]-alpha-methyl-1H-benzotriazole-1-acetate | 9D | 10D | 10D | 10D | 10D | 7IM |
| | 1I | 1I | 1D | 2CY | 0 | 1I |
| | 1I | 1I | 1I | 2I | 0 | 2I |
| Methyl 6-[(2-chloro-alpha, alpha,alpha-trifluoro-p-tolyl)oxy]-1H-benzotriazole-1-acetate | 9DI | 10D | 9DIM | 10D | — | — |
| Methyl 5-[(2-chloro-alpha, alpha,alpha,6-tetrafluoro-p-tolyl)oxy]-alpha-methyl-2H-benzotriazole-1-acetate | 10D | 8D | 2D | 3D | 1CP | 5AL |
| | 5I | 2D | 2D | 2CY | 1CY | 2I |
| | 3D | 1I | 0 | 2CY | 1CP | 1I |
| Methyl 5-[(2-chloro-alpha, alpha,alpha-trifluoro-p-tolyl)oxy]-alpha-methyl-2H-benzotriazole-1-acetate | 10D | 9D | 2ICY | 9D | — | — |
| | 10D | 9D | 0 | 10D | — | — |
| | 7D | 5DCI | 0 | 5D | — | — |
| | 8D | 6D | 0 | 3D | — | — |
| | 2AL | 3I | 0 | 0 | — | — |
| Methyl 5-[(2-chloro-alpha, alpha,alpha,6-tetrafluoro-p-tolyl)oxy]-alpha-methyl-1H-benzotriazole-1-acetate | 3I | 1I | 2I | 1I | 0 | 0 |
| | 1I | 2I | 1D | 1D 1I | 0 | |
| | 2I | 2I | 1D | 2D | 1I | 2I |
| Methyl 5-[(2-chloro-alpha, alpha,alpha-trifluoro-p-tolyl)-oxy]-alpha-methyl-1H-benzotriazole-1-acetate | 7I | 8I | 3I | 5D | — | — |
| | 3I | 3I | 0 | 0 | — | — |
| | 3I | 3I | 1D | 0 | — | — |
| | 3I | 5I | 0 | 0 | — | — |
| Methyl 5-[(2-chloro-alpha, alpha,alpha-trifluoro-p-tolyl)oxy]-1H-benzotriazole-1-acetate | 9D | 6IAIM | 0 | 5IAIM | — | — |
| | 1D | 0 | 2D | 1I | — | — |
| | 0 | 0 | 1D | 2I | — | — |
| | 2I | 0 | 1D | 3I | — | — |

What is claimed is:

1. A compound having the structure:

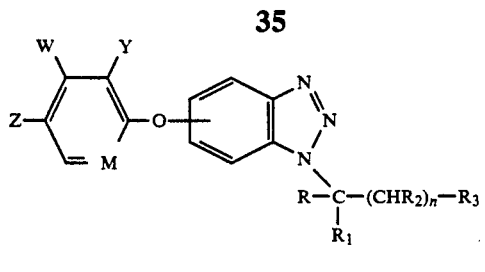

or

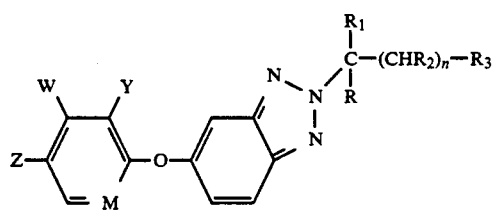

wherein

M is C—X,

W, X, Y and Z each independently represent hydrogen, halogen, nitro, cyano, $C_1$–$C_4$ haloalkyl or $C_1$–$C_4$ haloalkoxy;

n is 0, 1 or 2;

R is hydrogen, $C_1$–$C_4$ alkyl, aryl or when taken together with $R_1$, R and $R_1$ may form a ring in which $RR_1$ are represented by the structure —$(CH_2)_m$— where m is an integer of 2, 3, 4 or 5;

$R_1$ and $R_2$ are each independently hydrogen, $C_1$–$C_4$ alkyl or when taken together $R_1$ and $R_2$ may form a ring in which $R_1R_2$ are represented by the structure —$(CH_2)_m$— where m is an integer of 2, 3, 4 or 5;

$R_3$ is cyano,

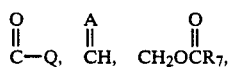

$CH_2OR_8$ or $CH(OR_9)_2$;

Q is OH, $OR_4$ or $NR_5R_6$;

A is O, $NOR_5$, $NCOR_5$, $NNR_5R_6$ or $NNHCONH_2$;

$R_7$ is hydrogen, $C_1$–$C_4$ alkyl or aryl;

$R_8$ is hydrogen, $C_1$–$C_4$ alkyl;

$R_9$ is $C_1$–$C_4$ alkyl;

$R_4$ is $C_1$–$C_6$ alkyl optionally interrupted by O or S or optionally substituted with $C_1$–$C_4$ alkoxy halogen, hydroxy, $C_3$–$C_6$ cycloalkyl, furyl, or optionally substituted phenyl; $C_3$–$C_6$ alkenyl optionally substituted with one or two $C_1$–$C_3$ alkoxy, halogen, substituted phenyl or $C_3$–$C_6$ cycloalkyl; $C_3$–$C_6$ alkynyl optionally substituted with $C_1$–$C_4$ alkoxy or halogen; $C_3$–$C_6$ cycloalkyl; ammonium; $C_1$–$C_6$ dialkylammonium; $C_1$–$C_6$ trialkylammonium; a metal cation; or a moiety of formula

$R_5$ and $R_6$ each independently represent hydrogen, $C_1$–$C_6$ alkyl, phenyl or halophenyl;

the benzotriazole N-oxide or N-methosulfate; and when $R_1$ or $R_2$ is $C_1$–$C_4$ alkyl, the optical isomer thereof, with the proviso that when M is C—X in formula I, wherein X is hydrogen, halogen, nitro, cyano or $C_1$–$C_4$ haloalkyl, the benzotriazole is substituted in the 6 position by aryloxy, n is O, $R_3$ is

and $R_7$ is $C_1$–$C_4$ alkyl, then R and $R_1$ cannot be hydrogen or $C_1$–$C_4$ alkyl.

2. The compound according to claim 1 having the structure:

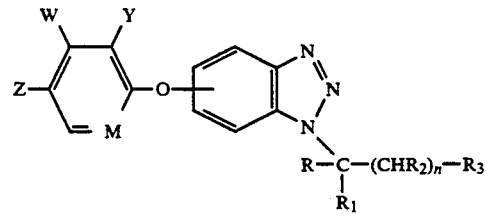

wherein the benzotriazole portion of said compound is substituted by aryloxy in the 5 or 6 position and M, Y, W, Z, n, R, $R_1$, $R_2$ and $R_3$ are as described in claim 1.

3. The compound according to claim 1 having the structure:

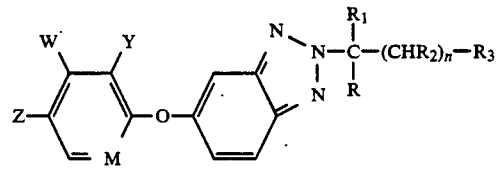

wherein M, Y, W, Z, n, R, $R_1$, $R_2$, and $R_3$ are as described in claim 1.

4. The compound according to claim 2 wherein the benzotriazole is substituted in the 6 position by aryloxy; M is C—X; W is hydrogen; X, Y, and Z each independently represent Cl, F, or $CF_3$; n is O; R is hydrogen or $C_1$–$C_4$ alkyl; $R_1$ is hydrogen or methyl; $R_3$ is

Q is OH or $OR_4$; and $R_4$ is $C_1$–$C_4$ alkyl.

5. The compound according to claim 2, methyl 6-[(2-chloro-α,α,α-trifluoro-p-tolyl)oxy]-1H-benzotriazole-1-acetate.

6. The compound according to claim 2, methyl 6-[(2-chloro-α,α,α-trifluoro-p-tolyl)oxy]-α-methyl-1H-benzotriazole-1-acetate.

7. The compound according to claim 2, 6-[(2-chloro-α,α,α,6-tetrafluoro-p-tolyl)oxy]-α-methyl-1H-benzotriazole-1-acetic acid.

8. The compound according to claim 2, methyl 6-[(2-chloro-α,α,α,6-tetrafluoro-p-tolyl)oxy]-α-methyl-1H-benzotriazole-1-acetate.

9. The compound according to claim 2, 6-[(2-chloro-α,α,α,6-tetrafluoro-p-tolyl)oxy]-β-methyl-1H-benzotriazole-1-propionic acid.

10. The compound according to claim 2, methyl 6-[(2-chloro-α,α,α,6-tetrafluoro-p-tolyl)oxy]-α,α-dimethyl-1H-benzotriazole-1-acetate.

11. The compound according to claim 2, methyl 6-[(ζ,α,α-trifluoro-2-nitro-p-tolyl)oxy]-α-methyl-1H-benzotriazole-1-acetate.

12. The compound according to claim 2, 6-[(2-chloro-α,α,α,6-tetrafluoro-p-tolyl)oxy]-α-methyl-1H-benzotriazole-1-acetamide.

13. The compound according to claim 2, isopropylammonium 7-[(2-chloro-α,α,α,6-tetrafluoro-p-tolyl)oxy]-α-methyl-1H-benzotriazole-1-acetate.

14. The compound according to claim 2, 6-[(2-chloro-α,α,α,6-tetrafluoro-p-tolyl)oxy]-α-methyl-1H-benzotriazole-1-acetonitrile.

15. A compound having the structure:

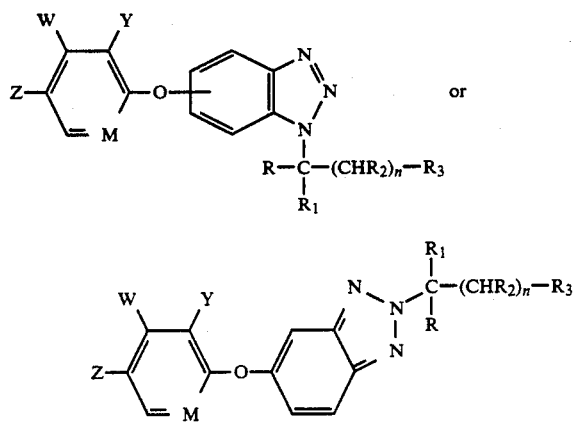

wherein
M is C—X;
W, X, Y and Z each independently represent hydrogen, halogen, nitro, cyano or $C_1$-$C_4$ haloalkyl;
n is 0, 1 or 2;
R is hydrogen, $C_1$-$C_4$ alkyl, or when taken together with $R_1$, R and $R_1$ may form a ring in which $RR_1$ are represented by the structure —$(CH_2)_m$— where M is an integer of 2, 3, 4 or 5;
$R_1$ and $R_2$ are each independnelty hydrogen, or $C_1$-$C_4$ alkyl;
$R_3$ si cyano,

or $CH_2OR_8$;
Q is OH, $OR_4$ or $NR_5R_6$;
$R_8$ is hydrogen or $C_1$-$C_4$ alkyl;

$R_4$ is $C_1$-$C_6$ alkyl optionally interrupted by O, or optionally substituted with $C_1$-$C_4$ alkoxy, halogen, hydroxy, $C_3$—$C_6$ cycloalkyl, or phenyl optionally substituted with one or two halogen or $C_1$-$C_3$ alkoxy; $C_3$-$C_6$ alkenyl optionally substituted with $C_1$-$C_4$ alkoxy or halogen; $C_3$-$C_6$ alkynyl optionally substituted with $C_1$-$C_4$ alkoxy or halogen; or $C_3$-$C_6$ cycloalkyl;

$R_5$ and $R_6$ each independently represent hydrogen, $C_1$-$C_6$ alkyl, phenyl or halophenyl;
the benzotriazole N-oxides, and when $R_1$ or $R_2$ is $C_1$-$C_4$ alkyl, the optical isomers thereof.

16. A method for the control of monocotyledonous and dicotyledonous annual, perennial and aquatic plant species which comprises applying to the foliage of said plants or to the soil or water containing seeds or other propagating organs of said plants, a herbicidally effective amount of a substituted aryloxy benzotriazole compound, wherein said compound is as described in claim 1.

17. The method according to claim 16, wherein said compound is 6-[(2-chloro-α,α,α,6-tetrafluoro-p-tolyl)oxy]-α-methyl-1H-benzotriazole-1-acetic acid.

18. The method according to claim 16, wherein said compound is methyl 6-[(2-chloro-α,α,α,6-tetrafluoro-p-tolyl)oxy]-α-methyl-1H-benzotriazole-1-acetate.

19. The method according to claim 16, wherein said compound is applied to the foliage of said plants at a rate of about 0.005 kg/ha to 5.0 kg/ha.

20. The method according to claim 16, wherein said compound is applied to the soil or water containing seeds, or other propagating organs, or said plants at a rate of about 0.5 kg/ha to 5.0 kg/ha.

21. A composition for controlling monocotyledonous and dicotyledonous annual, perennial and aquatic plant species comprising an agronomically acceptable carrier containing a herbicidally effective amount of a substituted aryloxy benzotriazole compound, wherein said compound is as described in claim 1.

22. The composition according to claim 21, wherein the carrier is liquid or solid in form.

23. The composition according to claim 22, which comprises about 5% to 25% by weight of the compound of claim 1, about 65% to 90% by weight of a carrier and about 5% to 10% by weight of a surface active agent.

24. The composition according to claim 22, which comprises about 80% to 97% by weight of a solid carrier and about 3% to 20% by weight of the compound of claim 1.

* * * * *

UNITED STATES PATENT AND TRADEMARK OFFICE
CERTIFICATE OF CORRECTION

PATENT NO. : 5,324,711
DATED : JUNE 28, 1994
INVENTOR(S) : DONALD R. NIELSEN, ET AL.

It is certified that error appears in the above-indentified patent and that said Letters Patent is hereby corrected as shown below:

Claim 1, Column 35, line 44:

should read --"$R_8$ is hydrogen or $C_1$-$C_4$ alkyl;" --

Claim 11, Column 37, line 2 and 3:
should read --"[($\alpha,\alpha,\alpha$-trifluoro-2-nitro-p-tolyl)oxy]-$\alpha$-methyl-1H-benzotriazole-1-acetate."--

Claim 13, Column 37, lines 7 and 9
should read --"The compound according to claim 2, isopropylammonium 6-[(2-chloro-$\alpha,\alpha,\alpha$, 6-tetrafluoro-p-tolyl)oxy]-$\alpha$-methyl-1H-benzotriazole-1-acetate."--

Claim 15, Column 37, line 41-43
should read --"$R_1$ and $R_2$ are each independently hydrogen, or
  $C_1$-$C_4$ alkyl;
 $R_3$ is cyano,"--

UNITED STATES PATENT AND TRADEMARK OFFICE
CERTIFICATE OF CORRECTION

PATENT NO. : 5,324,711
DATED : June 28, 1994
INVENTOR(S) : Donald R. Nielsen, et al It is certified that error appears in the above-indentified patent and that said Letters Patent is hereby corrected as shown below:

Claim 20, column 38, line 32
should read —"seeds, or other propagating organs, of said plants at"--

Signed and Sealed this

Eleventh Day of February, 1997

*Attest:*

BRUCE LEHMAN

*Attesting Officer*  *Commissioner of Patents and Trademarks*